US012791543B2

(12) United States Patent
Darrah et al.

(10) Patent No.: US 12,791,543 B2
(45) Date of Patent: Nov. 10, 2026

(54) SYSTEMS AND METHODS FOR MONITORING, QUANTITATIVE ASSESSMENT, AND CERTIFICATION OF LOW-CARBON HYDROGEN AND DERIVATIVE PRODUCTS

(71) Applicant: Koloma, Inc., Dublin, OH (US)

(72) Inventors: Thomas Darrah, Dublin, OH (US); Colin Whyte, Dublin, OH (US); Jacob Harrington, Dublin, OH (US); Brent Lary, Dublin, OH (US)

(73) Assignee: Koloma, Inc., Columbus, OH (US)

( * ) Notice: Subject to any disclaimer, the term of this patent is extended or adjusted under 35 U.S.C. 154(b) by 568 days.

(21) Appl. No.: 18/206,969

(22) Filed: Jun. 7, 2023

(65) Prior Publication Data

US 2023/0393114 A1 Dec. 7, 2023

Related U.S. Application Data

(60) Provisional application No. 63/349,888, filed on Jun. 7, 2022, provisional application No. 63/349,890, filed on Jun. 7, 2022.

(51) Int. Cl.
*G01N 33/24* (2006.01)

(52) U.S. Cl.
CPC ........... *G01N 33/241* (2013.01); *G01N 33/24* (2013.01)

(58) Field of Classification Search
CPC ............................ G01N 33/241; G01N 33/24
See application file for complete search history.

(56) References Cited

U.S. PATENT DOCUMENTS

| | | | |
|---|---|---|---|
| 4,382,912 | A | 5/1983 | Madgavkar et al. |
| 7,426,959 | B2 | 9/2008 | Wang et al. |
| 8,136,592 | B2 | 3/2012 | Hsu et al. |
| 2003/0010652 | A1 | 1/2003 | Hunt |
| 2004/0146288 | A1 | 7/2004 | Vinegar et al. |

(Continued)

FOREIGN PATENT DOCUMENTS

| | | | |
|---|---|---|---|
| CN | 214221410 | U | 9/2021 |
| CN | 114506817 | A | 5/2022 |
| WO | 2011034677 | A2 | 3/2011 |

OTHER PUBLICATIONS

Non-Final Office Action for U.S. Appl. No. 18/133,889 mailed Apr. 25, 2024.

(Continued)

*Primary Examiner* — John E Breene
(74) *Attorney, Agent, or Firm* — K&L Gates LLP

(57) ABSTRACT

A method for assessing a molecular or isotopic composition of a fluid includes analyzing a proportion of the fluid derived from a source to determine the source of the fluid, quantifying the proportion of the fluid derived from one or more sources, and assessing the relationships of chemical species within the fluid to validate the source of the fluid. This assessment can be accomplished through the direct measurement of molecular composition of fluid mixtures or the isotopic composition of specific fluids in that mixture, and/or a combination of statistical, thermodynamics, or kinetic modelling of these chemical reactions. The results of these measurements and models can be used to verify the source and conditions of various forms of hydrogen or other resources.

20 Claims, 6 Drawing Sheets

(56) References Cited

U.S. PATENT DOCUMENTS

| | | | |
|---|---|---|---|
| 2006/0185985 A1 | 8/2006 | Jones | |
| 2007/0298479 A1 | 12/2007 | Larter et al. | |
| 2008/0216774 A1 | 9/2008 | Fulton et al. | |
| 2009/0056941 A1 | 3/2009 | Valdez | |
| 2011/0220351 A1 | 9/2011 | Surguchev et al. | |
| 2012/0134749 A1* | 5/2012 | Darrah | E21B 49/087 405/80 |
| 2013/0113480 A1* | 5/2013 | Kadayam Viswanathan | G01V 3/32 324/303 |
| 2013/0233057 A1 | 9/2013 | Karoum et al. | |
| 2014/0114576 A1* | 4/2014 | Jain | G01V 11/00 702/9 |
| 2014/0250999 A1 | 9/2014 | Lawson | |
| 2015/0361833 A1 | 12/2015 | Hinders et al. | |
| 2017/0174512 A1 | 6/2017 | Oates et al. | |
| 2018/0066504 A1* | 3/2018 | Lawson | E21B 43/25 |
| 2019/0086287 A1* | 3/2019 | Rella | G01M 3/20 |
| 2020/0096663 A1 | 3/2020 | Shetty et al. | |
| 2021/0189856 A1* | 6/2021 | Gates | E21B 43/243 |
| 2021/0301658 A1 | 9/2021 | Zhang et al. | |
| 2022/0083048 A1 | 3/2022 | Cella et al. | |
| 2023/0050823 A1 | 2/2023 | Darrah et al. | |
| 2023/0323756 A1 | 10/2023 | Darrah et al. | |

OTHER PUBLICATIONS

Doveton, "Basics of Oil & Gas Log Analysis" [online], 1999 (1999) [retrieved on Jul. 24, 2023]. Retrieved from the internet: <URL:https://www.kgs.ku.edu/PRS/Info/pdf/doveton.PDF>.

International Search Report and Written Opinion dated Oct. 12, 2023 for PCT Application No. PCT/US2023/024711.

International Search Report and Written Opinion for International Application No. PCT/US2023/024723 mailed Oct. 24, 2023.

International Search Report and Written Opinion mailed Aug. 11, 2023 for PCT Application No. PCT/US2023/016610.

International Search Report and Written Opinion mailed Aug. 30, 2023 for International Application No. PCT/US2023/018331.

International Search Report and Written Opinion mailed Aug. 31, 2023 for International Application No. PCT/US2023/024719.

Invitation to Pay Additional Fees dated Aug. 14, 2023 for PCT Application No. PCT/US2023/024711.

Invitation to Pay Additional Fees for Internationa Application No. PCT/US2023/024723 , mailed Aug. 22, 2023.

Kelemen , et al., "Engineered carbon mineralization in ultramafic rocks for CO2 removal from Air: Review and New Insights", (2020). Chemical Geology, 550, 119628. https://doi.org/10.1016/j.chemgeo.2020.119628.

McQueen , et al., "Ambient weathering of magnesium oxide for CO2 removal from Air", (2020). Nature Communications, 11(1). https://doi.org/10.1038/s41467-020-16510-3.

Wang , et al., "Enhanced Hydrogen Production with Carbon Storage by Olivine Alteration in CO2-Rich Hydrothermal Environments." Journal of CO2 Utilitzation, vol. 30, 20219, pp. 205-213, https://doi.org/10.1016/j.jcou.2019.02.008.

Worman , et al., "Abiotic hydrogen (H2) sources and sinks near the Mid-Ocean Ridge (MOR) with implications for the subseafloor biosphere", (2020). Proceedings of the National Academy of Sciences, 117(24), 13283-13293. https://doi.org/10.1073/pnas.2002619117 Downloaded from https://www.pnas.org on Apr. 12, 2022.

Worman, Stacey Lynn, "Global Rates of Free Hydrogen (H2) Production by Serpentinization and other Abiogenic Processes within Young Ocean Crust", Department of Earth and Ocean Sciences Duke University, 2015.

* cited by examiner

SYSTEMS AND METHODS FOR MONITORING, QUANTITATIVE ASSESSMENT, AND CERTIFICATION OF LOW-CARBON HYDROGEN AND DERIVATIVE PRODUCTS

CROSS-REFERENCE TO RELATED APPLICATIONS

This application claims priority to U.S. Provisional Application No. 63/349,888 filed on Jun. 7, 2022, and claims priority to U.S. Provisional Application No. 63/349,890 filed on Jun. 7, 2022, the disclosure of each of which is incorporated herein in their entirety by this reference.

BACKGROUND

Embodiments of the present disclosure relate generally to the field of hydrogen, energy, production tax credits, carbon tax credits, chemical industry, chemical feedstock, forensic tracking, energy storage, carbon capture, carbon utilization, or carbon or natural gas storage. Some embodiments disclose methods of hydrogen or carbon verification and tracking. Hydrogen is a power source that has the potential to help reduce the usage of fossil fuels when combined with other sources. Hydrogen fuels are becoming more popular because they can be generated using sustainable energy sources such as geothermal, solar, wind, and hydroelectric power.

Further, determining the source of fluids and materials can be important to take advantage of tax credit programs. Specifically, determining and quantifying the eligibility of hydrogen for United States Internal Revenue Service 45V production tax credit programs, various Low Carbon Fuel Standards, or other production tax credit or subsidy programs, and determining and quantifying the eligibility of carbon dioxide storage for United States Internal Revenue Service 45Q tax credit programs or these other programs. As a result, determining and quantifying components of a fluid or reservoir can be important to businesses in various industrial sectors.

SUMMARY

Embodiments are directed to methods for assessing a molecular composition of a fluid and using chemical instruments to measure elements, molecules, isotopes, or isotopic ratios by visual inspection, quantitative analysis, or supervised or unsupervised computer-assisted machine learning to enable the identification and characterization of a source of the fluid either in a subsurface formation or in various chemicals, feedstocks, or energy sources at the surface.

In some examples, a method for assessing a molecular composition of a fluid can include analyzing a proportion of the fluid derived from a source to determine the source of the fluid, quantifying the proportion of the fluid, and assessing the relationships of chemical species within the fluid to validate the source of the fluid. In some examples, the fluid can include a gas or the mixture of gases including at least one of hydrogen, helium, a noble gas, ammonia, carbon dioxide, dihydrogen sulfide, nitrogen, or hydrocarbon gases. In some examples, analyzing a proportion of the fluid can include measuring elements, molecules, isotopes, or isotopic ratios to identify and characterize the source of the fluid. The source can include at least one of a geologic hydrogen, a subsurface formation, coal, steam methane reformation, pyrolysis, auto thermal reformation, chemical looping of gases, or electrolysis.

In some examples, the method can further include quantifying or apportioning a source of hydrogen in the fluid and certifying the source of hydrogen in the fluid. The source can include at least one of natural gas pipelines, hydrogen pipelines, oil pipelines, water pipelines, railcars, trucks, industrial and storage facilities, springs, surface seeps, subsurface reservoir, or boreholes for oil, natural gas, water, or hydrogen wells. In some examples, the method can further include monitoring for leaks or gas emissions in the least one of the sources. In some examples, the method can include validating and certifying a proportion of carbon dioxide stored in a subsurface reservoir and the form of the storage can include pore space or mineralization.

In some examples, the method can further include determining a residence time of the fluid in a subsurface formation. Determining a residence time can include analyzing a concentration of a noble gas and isotopic compositions of water, carbon dioxide, or other subsurface fluids, analyzing the timing of crystallization or recrystallization of minerals to derive the timing of hydrogen generation in the subsurface formation using a rock sample core, cutting, or outcrop, and analyzing the core, cutting, or outcrop to measure the uranium, thorium, potassium, and mineral composition and crustal noble gas content in the mineral to derive the timing of hydrogen generation in the subsurface formation. In some examples, the method can further include distinguishing the source of the hydrogen generation by timing the hydrogen generation in the subsurface formation. In some examples, the method can further include determining the gas saturation and gas to water ratio with respect to hydrogen, methane, natural gas, or carbon dioxide in the fluid, where the fluids are collected at the surface or from a subsurface formation.

A method for analyzing an isotopic composition can include analyzing a fluid to determine a source of the fluid, analyzing the fluid to determine a proportion of hydrogen feedstock derived from the source of the fluid, quantifying the proportion of hydrogen feedstock derived from the sources, and certifying the proportion of hydrogen feedstock derived from the sources. In some examples, the fluid can include at least one of hydrogen, helium, ammonia, carbon dioxide, dihydrogen sulfide, nitrogen, methane or hydrocarbon gas, water, methanol, synthetic fuels, ammonia, or carbon dioxide. The source can include at least one of a geologic hydrogen, coal, natural gas, biomass, ammonia, steel manufacturing, synthesis of chemicals, waste incineration, gas processing, atmospheric capture, natural gas pipelines, hydrogen pipelines, oil pipelines, water pipelines, railcars, trucks, steam methane reformation, pyrolysis, chemical looping, or electrolysis. In some examples, the method can further include validating and certifying the proportion of carbon dioxide stored in a subsurface reservoir including pore space or mineralization. In some examples, the method can further include determining carbon feedstock in a hydrogen carrier and quantifying the proportion of carbon derived from the hydrogen carrier. The hydrogen carrier can include at least one of coal combustion, natural gas combustion, biomass incineration, ammonia syntheses, steel manufacturing, chemical synthesis, waste incineration, and atmospheric capture. In some examples, analyzing the fluid can include comparing a measurement of an isotopic ratio of hydrogen from a sample with data for isotopic ratios of hydrogen for known samples of hydrogen. The method can further include certifying the source of hydrogen in at least one of a natural gas pipeline, hydrogen pipeline, oil pipeline, water pipeline, railcar, truck, or industrial facility. In some examples, the method also includes determining the composition of matter for hydrogen using the isotopic composition of hydrogen to determine, quantify, and validate a proportion of hydrogen, methane or other natural gases, or carbon dioxide derived from the source.

In some examples, a system for determining information including one or more characteristics of water, hydrogen, methane or other natural gases, carbon dioxide, or noble gases can include chemical analysis equipment configured to determine the information comprising at least one of: a molecular composition of a fluid including one or more of hydrogen, methane or other natural gases, or carbon dioxide; a gas saturation and gas to water ratio with respect to hydrogen, methane or other natural gases, or carbon dioxide; residence time of hydrogen or carbon dioxide in the fluid; a mass of water; a concentration of helium and other noble gases and isotopic concentrations of the helium or other noble gases; and a source of hydrogen, carbon dioxide, or natural gas. The system can also include a computing device operably connected to the chemical analysis equipment. In some examples, the computing device can be configured to electronically communicate the information to a remote computing device. In some examples, the remote computing device is operably coupled to the computing device. In some examples, the chemical analysis equipment includes at least one of an isotope ratio mass spectrometer, a cavity ring down spectroscopy apparatus, a residual gas analyzer, a quadrupole mass spectrometer, a radon detector, a scintillation counter, a gas chromatograph, a gas chromatograph fitted with a flame ionizing detector, and thermal conductivity detector.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the disclosure, wherein identical reference numerals refer to identical or similar elements or features in different views or embodiments shown in the drawings.

DETAILED DESCRIPTION

Figure 1:
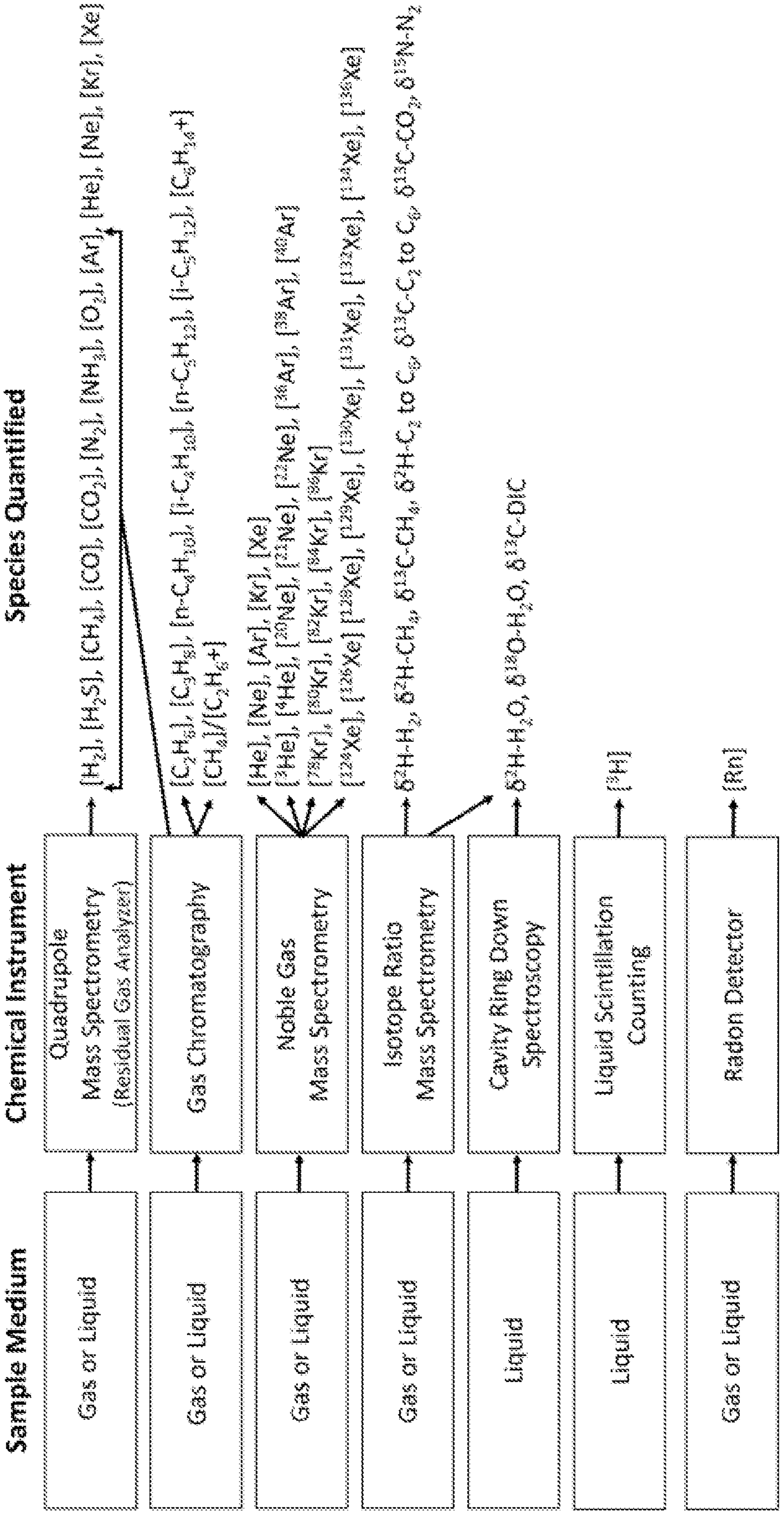
FIG. 1 is a list of analytical chemical instrumentation, the types of samples that can be analyzed with each instrument, and the elements and compounds that can be measured that are relevant to determining hydrogen and carbon dioxide sources, residence times, gas saturations, and temperatures of hydrogen formation, according to embodiments.

Embodiments of the present disclosure relate to systems and methods for using chemical instruments to measure elements, molecules, isotopes, or isotopic ratios by visual inspection, quantitative analysis, or supervised or unsupervised computer-assisted machine learning enable the identification and characterization of the source of hydrogen or carbon dioxide in the subsurface or various chemicals, in chemical feedstocks, in products derived using hydrogen as a feedstock (e.g., ammonia, methanol, synthetic fuels, renewable or low-carbon diesel, electrofuels, plastics, synthetic methane, various other electrofuels, or in processes that utilize other no-carbon or low-carbon hydrogen sources), or other energy sources at the surface. Analysis of the combination of chemical species forms the basis of the systems and methods used to determine the source of hydrogen. For example, the methods and systems herein can track and verify the source of naturally occurring hydrogen and other forms of hydrogen or carbon dioxide when sold as no-carbon or low-carbon hydrogen and track and verify chemical species for which hydrogen is used as a feedstock or incorporated into another chemical product (e.g., "green" ammonia, methanol, synthetic fuels, renewable or low-carbon diesel, electrofuels, plastics, synthetic methane, various other electrofuels, or in processes that utilize other no-carbon or low-carbon hydrogen sources).

Hydrogen as a chemical feedstock and fuel source used to replace hydrocarbons and other fossil fuels has been an unattained goal. Once formed, hydrogen provides a clean energy source that can eliminate greenhouse gases associated with direct use of fossil fuels as an energy source and the carbon burden produced from using hydrocarbons as a feedstock for hydrogen generation. As a result, various mechanisms for producing low-carbon or "blue" (e.g., steam methane reformation combined with carbon capture utilization and storage), "green" (e.g., electrolytic or methane pyrolysis by methods that do not emit carbon dioxide), and "gold" (e.g., hydrogen recovered from or produced within the earth) hydrogen can be included in various industrial sectors. Hydrogen is a very useful and important chemical that can be used in various industries. The present disclosure provides systems, methods and devices that address and provide solutions to the quantification, verification, and certification of low or carbon free hydrogen.

Geological hydrogen, native hydrogen, and natural hydrogen can be considered a potential energy source to transition to low carbon fuel. Methods and systems for the quantitative assessment and monitoring of the source of hydrogen and derivative products for which hydrogen is a feedstock, can include the measurement of molecular species (e.g., $H_2$, $N_2$, $NH_3$, CO, $CO_2$) or elemental gases (e.g., noble gases: He, Ne, Ar, Kr, Xe, Rn) and isotopes of gases (e.g., $\delta^2H—H_2$, $\delta^2H—CH_4$, $\delta^{13}C—CH_4$, $\delta^{13}C—CO_2$, $\delta^{15}N—N_2$, $^3He$, $^4He$, $^{20}Ne$, $^{21}Ne$, $^{22}Ne$, $^{36}Ar$, $^{38}Ar$, $^{40}Ar$, and their derivative isotopic ratios), water ($\delta^2H—H_2O$, $\delta^{18}O—H_2O$), or the concentrations of carbon dioxide or dissolved forms of carbon and their isotopic compositions (e.g., $\delta^{13}C$-DIC) sampled directly or indirectly from natural samples, chemical feedstocks, other industrial chemicals, or chemicals and products that used hydrogen and carbon feedstocks. Further, low-carbon sources of hydrogen can include hydrogen produced by electrolysis (e.g., using wind, solar, hydroelectric, or other forms of power to split water molecules into hydrogen and oxygen); methane pyrolysis or plasma reforming with partial oxidation (catalytic steam reforming from heavier hydrocarbons); chemical looping of gases from various sources (e.g., biomass, renewable natural gas, pressure swing absorption rejectate, refinery emissions, sewage treatment emissions), hydrogen produced from biological sources (e.g., archaea, bacterial), syngas ($H_2$+CO) formation from coal, oil, or petroleum coke; steam methane reformation, or the like, each with varying carbon intensities. Further gases, isotopes, or materials may be measured and analyzed according to the techniques disclosed herein.

The use of chemical instruments to measure elements, molecules, isotopes, or isotopic ratios by visual inspection, quantitative analysis, or supervised or unsupervised computer-assisted machine learning can enable the identification and characterization of hydrogen, hydrogen carriers, and products derived using hydrogen feedstocks. FIG. 1 is a list of analytical chemical instrumentation, the types of samples that can be analyzed with each instrument, and the elements and compounds that can be measured that are relevant to determining the genetic source of hydrogen, hydrogen carriers, and products derived using hydrogen feedstocks, according to embodiments. In some examples, the chemical analysis equipment includes at least one of an isotope ratio mass spectrometer, a cavity ring down spectroscopy apparatus, a residual gas analyzer or quadrupole mass spectrometer, a radon detector, a scintillation counter, a gas chromatograph, a gas chromatograph fitted with a flame ionizing detector, and thermal conductivity detector. It should be noted that additional chemical species and chemical equipment for detecting the same may be included with the chemical species and chemical equipment for detecting the chemicals species listed in FIG. 1.

The chemical analysis equipment can be used in a system for determining information including one or more characteristics of water, hydrogen, methane or other natural gases, carbon dioxide, or noble gases. In some examples, the system can include the chemical analysis equipment configured to determine the information comprising at least one of a molecular composition of a fluid including one or more of hydrogen, methane or other natural gases, or carbon dioxide, a gas saturation and gas to water ratio with respect to hydrogen, methane or other natural gases, carbon dioxide, a residence time of hydrogen or carbon dioxide in the fluid, a mass of water, a concentration of helium and other noble gases and isotopic concentrations of the helium or other noble gases, and a source of hydrogen, carbon dioxide, or natural gas.

Figure 2:
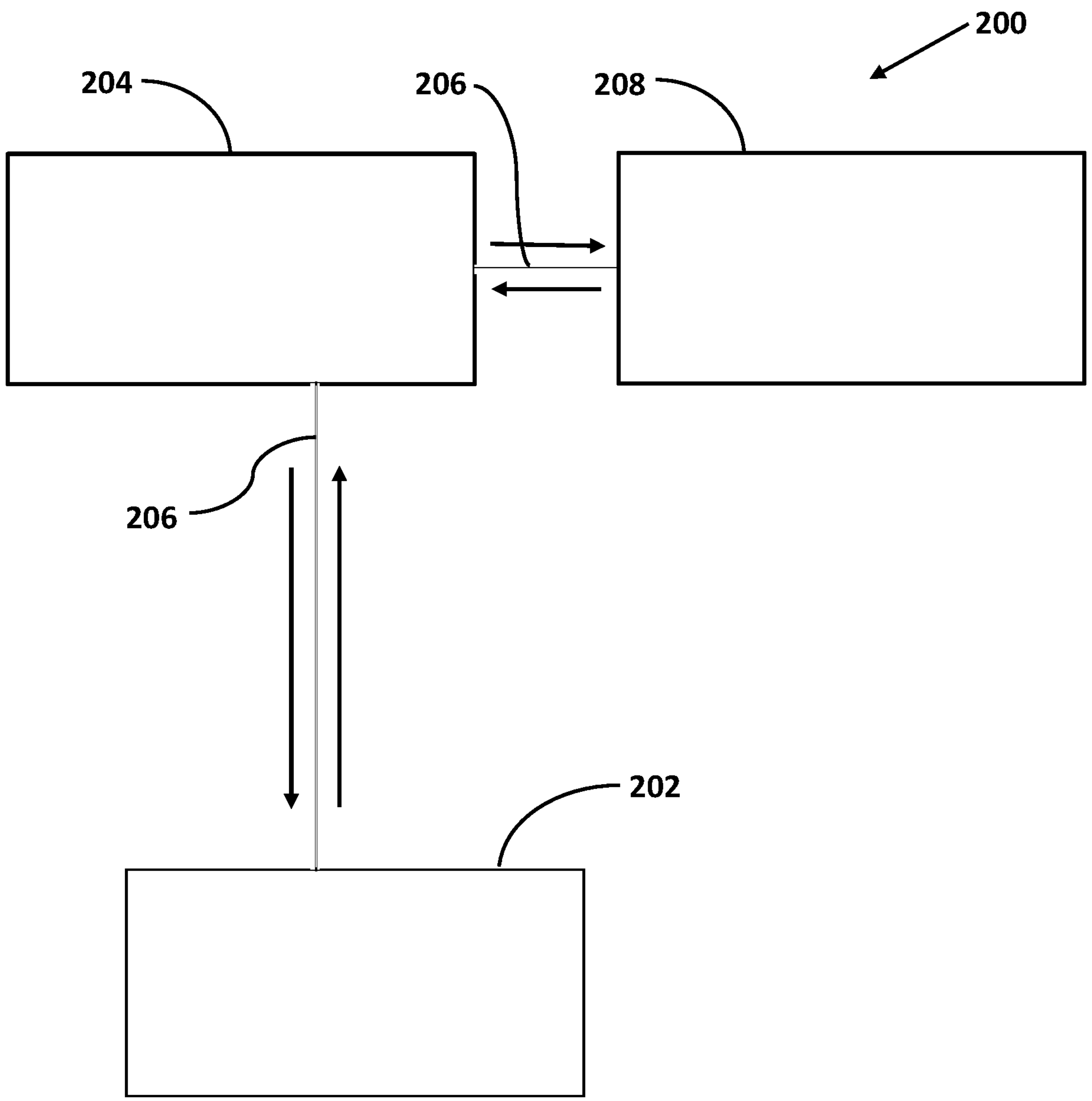
FIG. 2 is a block diagram of a system including analytical chemical instrumentation, a computing device, and a remote computing device, according to an embodiment.

FIG. 2 is a system 200 that includes analytical chemical instrumentation, a computing device 204, and a remote computing device 208, according to an embodiment. The system 200 is used for determining information including one or more characteristics of water, hydrogen, methane or other natural gases, carbon dioxide, or noble gases. The system 200 can be implemented with computers for analysis, quantification, and assessment locally and remotely. For example, the chemical analysis equipment 202 can be operated locally at a subsurface formation. The equipment 202 can communicate with a computing device 204 operably connected to the chemical analysis equipment. The computing device 204 may be in electronic communication with the chemical testing or measuring equipment 202 to receive the measurements and data therefrom. In some examples, the computing device 204 can include a communication interface 206 configured to send notifications, reports, or data to other electronic devices. The computing device 204 can be operably coupled to a remote computing device 208. For example, the computing device 204 may be configured to send notifications and/or data at a selected radio frequency, via BLUETOOH, or via WI-FI to a remote electronic device or remote computer 208. In some examples, the computing device 204 can transmit a signal wirelessly to the remote electronic device or computer 208 and provide an indication directly to the electronic device 208. In some embodiments, the measurements may be transferred via a memory storage device (e.g., flash drive, disc, or the like). The computing device 204 may fetch data for comparison to sample measurement data from one or more data libraries.

Figure 3:
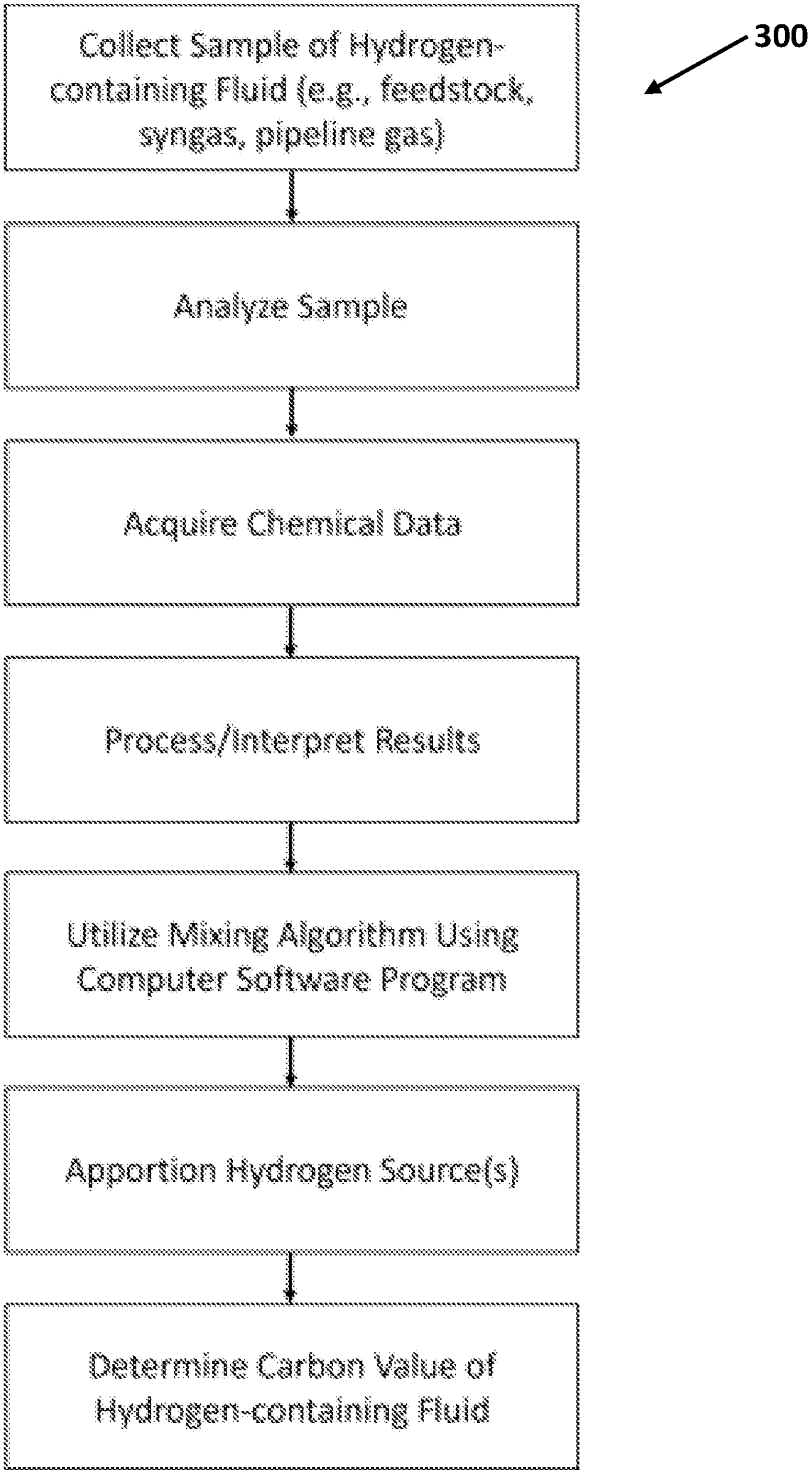
FIG. 3 is a flowchart of a method for determining properties of a fluid, according to an embodiment.

FIG. 3 is a flowchart of a method 300 for determining properties of a fluid, according to an embodiment. The method 300 includes collection of hydrogen-containing fluids, chemical analyses on the collected fluid, chemical data acquisition, interpretation of the chemical data, and apportioning the sources of hydrogen within the fluid sample, which can be used to determine the carbon credit value of the fluid, according to an embodiment. Some or all of the blocks shown in FIG. 3 may be utilized in one or more embodiments. For example, methods and systems for assessing a molecular composition of a fluid can be conducted. Specifically, identifying and characterizing hydrogen, whether as a gas or compressed to a liquid, and its derivative products can be important analysis for determining feasibility and productivities in energy production. In some examples, the fluid can include a gas or the mixture of gases, such as those including at least one of hydrogen, helium, a noble gas, ammonia, carbon dioxide, dihydrogen sulfide, nitrogen, or hydrocarbon gases.

The methods and systems disclosed herein can apply to at least hydrogen from inputs and offtakes of natural gas in pipelines; inputs and offtakes of natural gas transported by other means (e.g., trucking, railcar, pipelines); biologically- or organically-derived hydrogen or molecules containing hydrogen; hydrogen formed by electrolysis; methane pyrolysis or plasma reforming with partial oxidation; chemical looping of gases; hydrogen produced from biological sources (e.g., archaea, bacterial); syngas synthetic/electrofuels containing hydrogen; synthetic plastics, prospective leaks or fugitive or stray natural gas investigations involving hydrogen; storage in subsurface reservoirs, formations, caverns, or other facilities; or usage in other industrial facilities (e.g., refineries, ammonia plants, synthetic/electrofuels generators, synthetic plastic manufacturing, direct reduced steel manufactured, or high grade heat), among others.

Methods and systems herein provide for the analyzing a proportion of the fluid derived from a source to determine the source of the fluid or components therein. In some examples, analyzing a proportion of the fluid comprises measuring elements, molecules, isotopes, or isotopic ratios to identify and characterize the source of the fluid. The methods disclosed herein can further include a quantitative assessment and monitoring of the source of hydrogen and derivative products for which hydrogen is a feedstock, which can be performed using measurement(s) of one or more chemical species, elemental gases, isotopes of gases, isotopes of water, or the concentrations of carbon dioxide or dissolved forms of carbon and their isotopic compositions sampled directly or indirectly from natural samples, chemical feedstocks, or other industrial chemicals.

In some examples, the source and proportion of various hydrogen supplies can be determined and verification of low-carbon hydrogen status. For example, the source can include at least one of a geologic hydrogen, a subsurface formation, coal, steam methane reformation, pyrolysis, autothermal reformation, chemical looping of gases, or electrolysis. Other sources can include electrolytic, pyrolysis, geological, biological, or carbon reduction through chemical looping.

The analysis can be conducted for at least the United State Internal Revenue Service 45V production tax credit; various Low Carbon Fuel Standards; or other incentive, subsidy, or tax credit programs and can enable low-carbon or "green" certification of hydrogen and tracking of "green" hydrogen and derivative chemicals for which hydrogen is a feedstock. Hydrocarbon gases can be formed naturally by inorganic or biological processes that can result in distinct molecular and stable isotopic signatures of methane (e.g., $\delta^2H—CH_4$, $\delta^{13}C—CH_4$) and hydrocarbon species of higher molecular weight hydrocarbon species (e.g., $\delta^2H—C_2$, $\delta^{13}C—C_2$). Thermogenic hydrocarbons (e.g., oil, shale gas) can be formed from the thermocatalytic cracking of organic matter and result in $S^2H—CH_4$ generally greater than about −250‰ and $\delta^{13}C—CH_4$ generally between about −55‰ and −25‰. As thermal maturity of the organic matter increases, the stable isotopic signatures of carbon and hydrogen in the produced hydrocarbons can become more positive in predictable fashions. In contrast, microbial methane (e.g., coal-bed methane) can be formed from methanogenic archaea utilizing the reduction of $CO_2$ or fermentation of acetate in the shallow subsurface, which result in $\delta^{13}C—CH_4$ values generally less than about −55‰ and $\delta^2H—CH_4$ values generally greater than about −250‰ but less than about −100‰. Abiotic methane can be the result of Sabatier reactions between $H_2$ and $CO_2$ at elevated (about 150° C. or more) temperatures and may be observed in geothermal systems, which result in isotopically heavy $\delta^{13}C—CH_4$ (about −20‰ or more) and $\delta^2H—CH_4$ (about −400‰ or more).

Hydrogen can be formed by inorganic or biological processes. The isotopic composition of hydrogen generated by either mechanism displays molecular or isotopic characteristics that can be used to determine the source of hydrogen. For example, like microbial methane, hydrogen produced by biological species is associated with highly elevated levels of dissolved inorganic carbon and dissolved inorganic carbon that is isotopically enriched (e.g., $\delta^{13}C$-DIC greater than about −10‰) relative to that produced from $CO_2$ dissolution or the oxidation of organic matter (e.g., $\delta^{13}C$-DIC commonly ranging from −30‰ to −10‰). Hydrogen produced by microbes also displays hydrogen isotopic compositions that are significantly depleted in deuterium relative to protium (e.g., $\delta^2H-H_2$ less than about −750‰).

The most dominant geologic process that produces natural hydrogen is the serpentinization of iron-rich minerals such as olivine and pyroxene, which are minerals most-commonly found in mantle-derived mafic and ultramafic igneous rocks (e.g., basalt, gabbro, and peridotite). Olivine and pyroxene minerals also contain trapped $^3He$, therefore a fluid rich in hydrogen produced from serpentinization may be enriched in $^3He$ relative to other crust-derived or microbially-derived hydrogen-rich fluids. This is most often observed in geothermal environments but has also been seen in intracontinental settings where mafic and ultramafic igneous rocks have intruded and elevated natural hydrogen has been found. Further, while carbon dioxide has many sources in the crust (e.g., microbial respiration, dissolution of calcium carbonates, post-mature kerogen), mantle-derived fluids have characteristic $\delta^{13}C—CO_2$ (about −2‰ to −8‰) and $[CO_2]/[^3He]$ ratios (about $1\times10^9$ to $10\times10^9$). Mantle-derived helium displays a $[^3He]/[^4He]$ of up to about 6 to $8R_A$ (where $R_A$ is the $[^3He]/[^4He]$ in air or $1.384\times10^{-6}$) or higher in mantle plume environments, while the helium isotopic ratio in the atmosphere is about IRA and the helium isotopic ratio of crustal gases is about $0.02R_A$. Together, these geochemical signatures can be used as evidence for identifying the source of naturally occurring hydrogen in the subsurface. In most crustal systems, the relative contributions of each component can be resolved using a combination of helium, neon, or argon isotopes or various ratios of helium or other noble gases to other atmospheric noble gases (e.g., He/Ne, He/Ar, He/Kr, He/Xe, or to specific isotopes of one of these elements).

Figure 4:
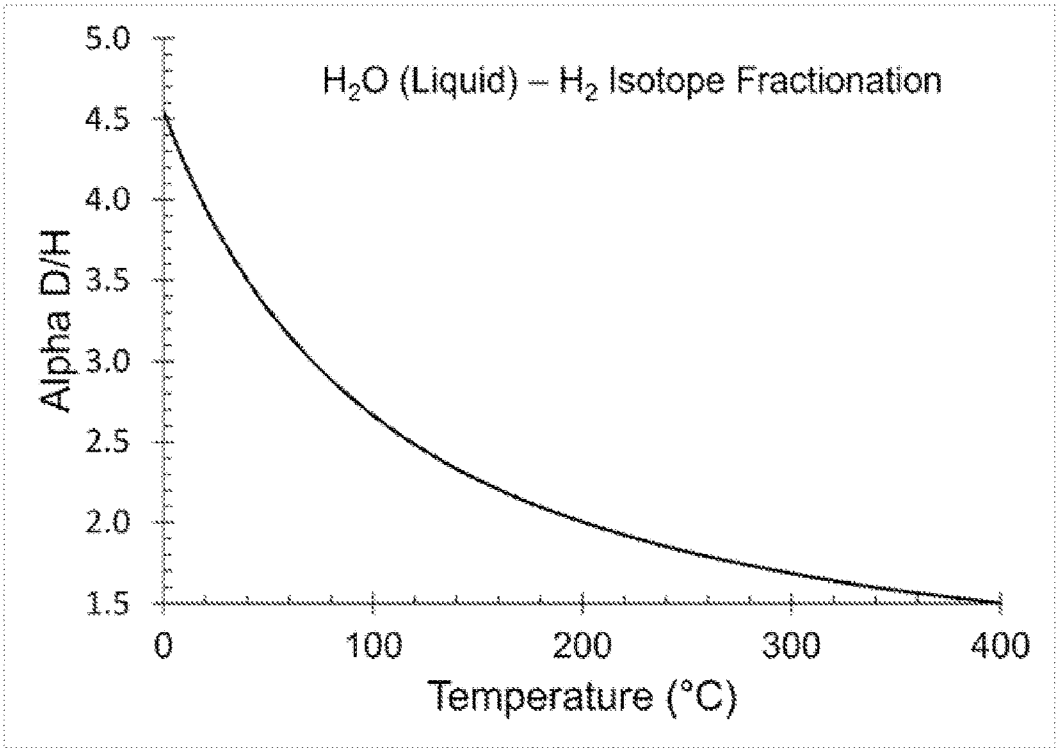
FIG. 4 is a graph of the degree of fractionation between hydrogen isotopic compositions of liquid water and molecular hydrogen as a function of temperature in the paired liquid water-molecular hydrogen system that occurs during the serpentinization process.
Figure 5:
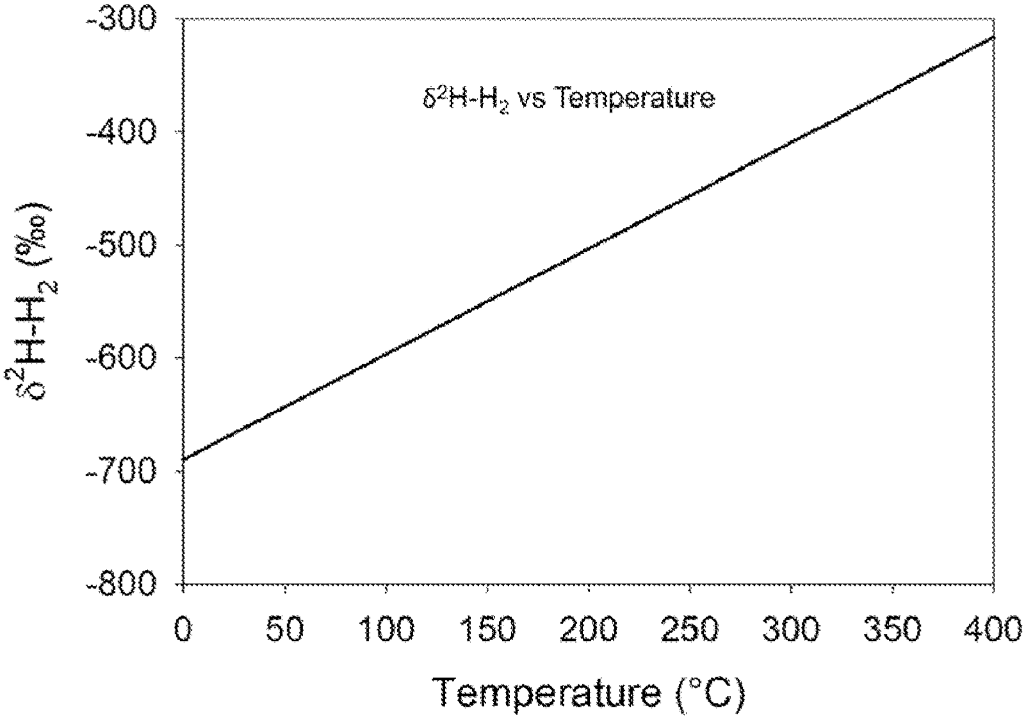
FIG. 5 is a graph of the relationship between the isotopic composition of molecular hydrogen and temperature of hydrogen formation during the serpentinization process.

Hydrogen produced by various inorganic processes displays a predictable relationship with temperature and the original source of water from which hydrogen is derived, as shown in FIGS. 4 and 5. FIG. 4 is a graph of the degree of fractionation (e.g., alpha or the fractionation factor) between hydrogen isotopic compositions of liquid water ($\delta^2H—H_2O$) and molecular hydrogen ($\delta^2H—H_2$) as a function of temperature in the paired liquid water-molecular hydrogen system that occurs during the serpentinization process. Similar graphs for other hydrogen-forming reactions, such as pyritization, which quantifies the degree of fractionation between a given reactant and the hydrogen product (e.g., dihydrogen sulfide and hydrogen) are also conceived of as part of embodiments. Because hydrogen can be formed by the reduction of water by a variety of mechanisms (e.g., serpentinization), there is a strong temperature-fractionation relationship for $H_2O—H_2$ systems. For example, thermochemical calculations can show that in very reducing conditions (e.g., low oxygen fugacity) fractionation factors between oxygen and hydrogen during the olivine-water or pyroxene-water interactions, such as serpentinization, are well calibrated from temperatures ranging from about 20° C. to 700° C. As a result, if the $\delta^2H—H_2O$ and $\delta^2H-H_2$ values of a given water-$H_2$ gas pair can be measured, or if the $S^2H—H_2$ values of a fluid containing hydrogen can be measured while the isotopic composition of the original water can be reasonably assumed, the temperatures of gas formation can be calculated based on measuring the $S^2H—H_2$ and calculating the temperature-dependent degree of fractionation relative to the original hydrogen-carrying molecule. For example, if the $S^2H—H_2O$ value is known, either based on local porewater isotopic values, seawater isotopic values, or known isotopic composition of water sources used in electrolysis or other reactions. These calculated temperatures can be compared to local geothermal gradients to determine the genetic source of natural hydrogen gas and by comparison to a range of parameters (e.g., concentration of other gases, concentration of dissolved inorganic carbon, mineralogy) to determine the mechanism responsible for the formation of hydrogen, such as serpentinization or pyritization.

FIG. 5 is a graph of the relationship between the isotopic composition of molecular hydrogen ($\delta^2H—H_2$) and temperature of hydrogen formation during the serpentinization process. Similar graphs for other hydrogen-forming reactions (e.g., pyritization) that quantify the degree of fractionation between a given reactant and the hydrogen product (e.g., dihydrogen sulfide and hydrogen) are also conceived of as part of embodiments. A small amount of re-equilibration between ambient $H_2O$ and $H_2$ can be expected above 100° C. in higher temperature regimes, suggesting these calculated temperatures may represent a minimum. Whether plotted manually, with a computer, or by other form of graphing or statistical tool, graphs of $\delta^2H—H_2$ can be plotted relative to either water isotope data ($\delta^2H—H_2O$) or calibration lines of anticipated temperature based on the thermodynamics of equilibrium between water and newly generated hydrogen gas assuming a fractionation factor between the two species that is dependent on mineralogy, porewater chemistry, and temperature.

Natural hydrogen can also be produced by biologically-mediated (e.g., bacterial production) or other inorganic processes, including magma oxidation, basalt alteration, magmatic degassing, cataclasis, pyritization ("metal-sulfide precipitation")), lava crystallization, radiolysis, graphitization, and lava-seawater interactions. For those reactions that involve interactions with water (e.g., magma oxidation, basalt alteration, low-temperature weathering, magma crystallization, lava-seawater interactions), there is a similarly predictable, temperature-dependent relationship between the original source of water and the derived hydrogen. In this case, the same process described for serpentinization can be applied and used to determine the source of hydrogen. For other mechanisms, similar thermodynamic relationships exist between the original hydrogen-containing molecule, such as dihydrogen sulfide in pyritization ("metal-sulfide precipitation"), methane or other heavier molecular weight hydrocarbons in graphitization, water in radiolysis or cataclasis, or hydroxyls in radiolysis or cataclasis, and the evolved hydrogen. For example, thermodynamic calculations show that fractionation factors between dihydrogen sulfide and hydrogen formed during the olivine-dihydrogen sulfide or pyroxene-dihydrogen sulfide reaction (e.g., pyritization ("metal-sulfide precipitation")) are well-calibrated according to temperature ranging from about 20° C. to 700° C. As a result, if the $\delta^2H—H_2S$ and $\delta^2H—H_2$ values of a given $H_2S—H_2$ (gas) pair can be measured, or if the $\delta^2H—H_2$ values of a fluid containing hydrogen can be measured while the isotopic composition of the original dihydrogen sulfide can be reasonably assumed, the temperatures of gas formation can be calculated based on measuring the $\delta^2H—H_2$ and calculating the temperature-dependent degree of fractionation relative to the original hydrogen-carrying molecule. These calculated temperatures and a range of parameters can be used to determine mechanism responsible (e.g., genetic source) for the formation of hydrogen (e.g., pyritization compared to serpentinization) especially when compared to other geochemical parameters (e.g., concentration of other gases, concentration of dissolved inorganic carbon, mineralogy) and the source rock of the hydrogen gas based on a comparison to the local geothermal gradient. Whether plotted manually, with a computer, or by another form of graphing or statistical tool, graphs of $\delta^2H—H_2$ can be plotted relative to either the isotopic composition of the hydrogen-carrying molecule (e.g., $\delta^2H—H_2S$) or calibration lines of anticipated temperature based on the thermodynamics of equilibrium between the hydrogen-carrying molecule and newly generated hydrogen gas assuming a fractionation factor between the two species that is dependent on mineralogy, porewater chemistry, and temperature.

The concentrations of other gases and chemical species (e.g., $H_2$, $N_2$, $NH_3$, CO, $CO_2$; noble gases: He, Ne, Ar, Kr, Xe, Rn; and the isotopes of these gases (e.g., $\delta^2H—CH_4$, $\delta^{13}C—CH_4$, 6° C.—$CO_2$, $\delta^{15}N—N_2$, $^3He$, $^4He$, $^{20}Ne$, $^{21}Ne$, $^{22}Ne$, $^{36}Ar$, $^{38}Ar$, $^{40}Ar$, among others)) can also be used to differentiate hydrogen formed by various synthetic processes, electrolysis (e.g., using wind, solar, hydroelectric, or other forms of power to split water molecules into hydrogen and oxygen); methane pyrolysis or plasma reforming with partial oxidation (catalytic steam reforming from heavier hydrocarbons); chemical looping of gases from various sources (e.g., biomass, renewable natural gas, pressure swing absorption rejectate, refinery emissions, sewage treatment emissions), hydrogen produced from biological sources (e.g., archaea, bacterial), syngas ($H_2$+CO) formation from coal, oil, or petroleum coke; steam methane reformation, or the like, each with varying carbon intensities. This technique can distinguish sources of hydrogen based on the measurable abundances of common tracers (e.g., $CH_4$, $N_2$, $^4He$, Ne, Ar, Kr, Xe) and their isotopic values (e.g., $\delta^2H—CH_4$, $\delta^{13}C—CH_4$, $\delta^{13}C—CO_2$, $\delta^{15}N—N_2$, $^3He$, $^4He$, $^{20}Ne$, $^{21}Ne$, $^{22}Ne$, $^{36}Ar$, $^{38}Ar$, $^{40}Ar$, among others) compared to anticipated values. In each process, temperature, pressure, and salinity dependent variables can dictate the predictable degree of the fractionation in gas tracers throughout the hydrogen synthesis process and later gas separation or purification processes. For example, during the membrane separation, pressure-swing absorption, or cryogenic separation, these and other chemical species are predictably separated. The physicochemical parameters (e.g., temperature, pressure, and salinity) can be used to determine initial compositions, apportion the amount of hydrogen sourced from various natural and synthetic formation mechanisms, or certify the source of hydrogen. For example, hydrogen formed by methane steam reforming that is later processed for carbon capture utilization and storage exhibits predictable fractionation of chemical species that be used to determine the source, apportion the amount of hydrogen sourced from various natural and synthetic formation mechanisms, or certify the source of hydrogen. Whether plotted manually, with a computer, or by other form of graphing or statistical tool, graphs of $\delta^2H—H_2$ can be plotted relative to either water isotope data ($\delta^2H—H_2O$) or calibration lines of anticipated temperature based on the thermodynamics of equilibrium between water and newly generated hydrogen gas assuming a fractionation factor between the two species that is dependent on mineralogy, porewater chemistry, and temperature.

Hydrogen can also be produced by various synthetic processes, including electrolysis (e.g., using wind, solar, hydroelectric, or other forms of power to split water molecules into hydrogen and oxygen); methane pyrolysis or plasma reforming with partial oxidation (catalytic steam reforming from heavier hydrocarbons); chemical looping of gases from various sources (e.g., biomass, renewable natural gas, pressure swing absorption rejectate, refinery emissions, sewage treatment emissions), hydrogen produced from biological sources (e.g., archaea, bacterial), syngas ($H_2$+CO) formation from coal, oil, or petroleum coke; steam methane reformation, or the like, each with varying carbon intensities. For those reactions, there is a similarly predictable, temperature-dependent relationship between the original source of the hydrogen-carrying molecule (e.g., water, methane) and the derived hydrogen. Like the natural processes described above, in other synthetic processes (e.g., electrolysis, pyrolysis), the temperatures calculated from chemical measurements (e.g., chemical abundances or their isotopic composition) can be compared to known sources of water, methane, or other forms of natural gas, dihydrogen sulfide, or other hydrogen carries and temperatures of reactions to determine the source of synthetic hydrogen produced by various reactions or other reactions that utilize these hydrogen-carrying molecules. Thus, by comparison to measured, known, or assumed compositions of source waters, sources of methane or other forms of natural gas, or sources of dihydrogen sulfide and temperature ranges of affiliated reactions, the source of hydrogen can be identified, apportioned or certified as green (e.g., formed by electrolysis), blue (e.g., formed steam methane reformation with carbon capture utilization, and storage; methane pyrolysis), gold (e.g., natural hydrogen formed by various mechanisms), or others forms of hydrogen synthesis. In addition to isotopic measurements, a range of parameters (e.g., concentration of other gases (e.g., $H_2$, $N_2$, $NH_3$, CO, $CO_2$; noble gases: He, Ne, Ar, Kr, Xe, Rn; and the isotopes of these gases (e.g., $\delta^2H$—$CH_4$, $\delta^{13}C$—$CH_4$, $\delta^{13}C$—$CO_2$, $\delta^{15}N$—$N_2$, $^3He$, $^4He$, $^{20}Ne$, $^{21}Ne$, $^{22}Ne$, $^{36}Ar$, $^{38}Ar$, $^{40}Ar$, among others)), can be used to determine the source of hydrogen formed by various processes. Whether plotted manually, with a computer, or by other form of graphing or statistical tool, graphs of $\delta^2H$—$H_2$ can be plotted relative to either water isotope data ($\delta^2H$—$H_2O$) or other hydrogen-carrying molecules (e.g., methane: $\delta^{13}C$—$CH_4$; $\delta^2H$—$CH_4$ or other forms of natural gases (e.g., $\delta^{13}C$—$C_2H_6$; $\delta^2H$—$C_2H_6$), or dihydrogen sulfide (e.g., $\delta^2H$—$H_2S$)) or calibration lines of anticipated temperature based on the thermodynamics of equilibrium between water and newly generated hydrogen gas assuming a fractionation factor between the two species that is dependent on temperature, pressure, and salinity. A computer executed software program including a mixing algorithm may be utilized to model the mixture of species in the sample (e.g., fractionation factor) based on the chemical data acquired by the analyses disclosed herein.

The same thermodynamic calculations and measurements can be applied and used to determine the source of hydrogen and delineate the process used to synthesize hydrogen formation. These same chemical parameters can be used to determine the mechanism responsible (e.g., source) for the formation of hydrogen (e.g., steam methane reforming, electrolysis, and pyrolysis, purified by chemical looping, as compared to various forms of natural hydrogen) especially when in combination with other geochemical parameters (e.g., concentration of other gases). Whether plotted manually, with a computer, or by another form of graphing or statistical tool, graphs of $\delta^2H$—$H_2$ can be plotted relative to either the isotopic composition of the hydrogen-carrying molecule (e.g., $\delta^2H$—$H_2O$, $\delta^{13}C$—$CH_4$, $\delta^2H$—$CH_4$, $\delta^2H$—$H_2S$) or calibration lines of anticipated temperature based on the thermodynamics of equilibrium between the hydrogen-carrying molecule and newly generated hydrogen gas assuming a fractionation factor between the two species that is dependent on temperature, pressure, and salinity. These techniques can be used to determine, apportion, or certify natural hydrogen ("gold hydrogen") or other synthetic forms of hydrogen.

In some embodiments, characteristics such as the concentration of methane compared to the concentration of hydrogen (e.g., $[CH_4]/[H_2]$), can help provide important information as to the origin of natural hydrogen. Generally, as the temperature increases, the kinetic rate of the Sabatier reaction converts more hydrogen to methane in the presence of ambient gaseous or dissolved carbon dioxide. During this process, the newly formed methane (e.g., abiogenic methane) can have unique isotopic compositions (e.g., $\delta^{13}C$—$CH_4$ greater than −20‰). As a result, a generally positive correlation between $[CH_4]/[H_2]$ and $\delta^2H$—$H_2$ or $\delta^{13}C$—$CH_4$ can be taken as an indication of increasing temperature of gas formation (and vice versa). Whether plotted manually, with a computer, or by other form of graphing or statistical tool, graphs of these data can be used to determine temperature and resolve the mixing of multiples sources or generations of gas. In some embodiments, a system and method for determining the source of hydrogen can derive or infer the source based on determining the temperature of hydrogen formation. By determining the thermal conditions ("genetic source") of hydrogen, hydrogen production can be monitored, the fate of fugitive hydrogen can be tracked, or a "fingerprint" of natural hydrogen can be identified that can be used to track its utilization in various commercial processes. For example, determining the thermal conditions at which hydrogen from an industrial facility was formed may allow the determination of which natural hydrogen reservoirs the facility sources from.

In some embodiments, accurately determining the source may be important in evaluating the likelihood that hydrogen formed at a specific depth would migrate into a specific reservoir or be emplaced below a specific seal and/or in estimating the volume of gas that would accumulate in a given 3-dimensional trap. The source fingerprint may be important for various efforts to apportion the source of gas, identify chemicals derived that use this or other forms of hydrogen as a feedstock, or track its downstream utilization or environmental fate. In some embodiments, as the source fingerprint can also be used to identify, apportion, or verify or authenticate its qualification for the United States Internal Revenue Service 45V production tax credit, various Low Carbon Fuel Standards, and various other hydrogen subsidy, incentive, or credit programs.

In some embodiments, for classification of hydrogen, one or more of a suite of geochemical analyses may be conducted on a fluid sample(s) or from samples collected from various other sources of hydrogen formation. Fluid samples can be taken from a well at one or more depths or may be taken from the surface. Adequate sample containers for gas samples can include refrigeration-grade copper tubes sealed with brass, steel, or other forms of refrigeration clamps; seamless stainless-steel cylinders; Isotubes®; gas-tight septum vials, or the like. The fluid may be extracted from the sample container on a vacuum line and, if necessary, may be sonicated (e.g., for about 30 minutes) to ensure complete transfer of dissolved gases from the extraction vessel to the sample inlet line.

Major gas/dissolved gas components (e.g., $H_2$, $N_2$, $NH_3$, CO, $CO_2$, $C_1$-$C_6$+) in the sample can be measured by a Residual Gas Analyzer (RGA), Quadrupole Mass Spectrometer, gas-source mass spectrometers, a Gas Chromatograph (GC) fitted with a Flame Ionizing Detector (FID) and Thermal Conductivity Detector (TCD), or other suitable analytical equipment and techniques. Noble gases and their stable isotopes can be measured by a gas source mass spectrometer, such as following purification of an aliquot of the sample, cavity ringdown, or other suitable technique. The stable isotopic composition of gas molecules (e.g., $\delta^2H$—$H_2$, $\delta^2H$—$CH_4$, $\delta^{13}C$—$CH_4$, $\delta^{13}C$—$CO_2$, $\delta^{15}N$—$N_2$) can be measured by an isotope ratio mass spectrometer (IRMS), cavity ring down spectroscopy, or another suitable method. The IRMS can be used to also measure the stable isotopes of hydrogen and oxygen in water (e.g., $\delta^2H$—$H_2O$, $\delta^{18}O$—$H_2O$). Any other technique disclosed herein may be utilized to measure isotopes in fluid samples.

Determining the characteristics of hydrogen, carbon, or any other material in a subsurface geological formation may include collecting a fluid sample from a borehole or well. The borehole or well may be drilled for the characterization. The sample may be collected at the surface, such as from a water or other fluid source at the surface. For example, determining the characteristics of hydrogen, carbon, or any other material in other forms of gases may include retrieving a fluid sample from various inputs and outputs of processes that make synthetic hydrogen (e.g., electrolysis, pyrolysis, chemical looping), collected from various mechanisms of hydrogen transport (e.g., pipelines, trucks, cryogenic trucks, tanks, or other forms), storage (e.g., tanks, tube trailers, salt caverns, subsurface gas storage reservoirs, or collected in chemicals for which various forms of hydrogen were utilized as feedstocks (e.g., ammonia, methanol, synthetic fuels, renewable or low-carbon diesel, electrofuels, plastics, synthetic methane, various other electrofuels, or in processes that utilize other no-carbon or low-carbon hydrogen sources, synthetic plastics, or other energy sources at the surface). The sample may be analyzed or tested as set forth above to acquire chemical data. The chemical data (e.g., measurements) may be compared to measurements from known samples or standards using any of the analytical techniques disclosed herein. The comparison may be carried out on a computing device using electronic instructions to carry out any of the analytical techniques disclosed herein. For example, software may be utilized to automatically carry out any of the analytical techniques disclosed herein. Such comparisons may be carried out in real time.

Figure 6:
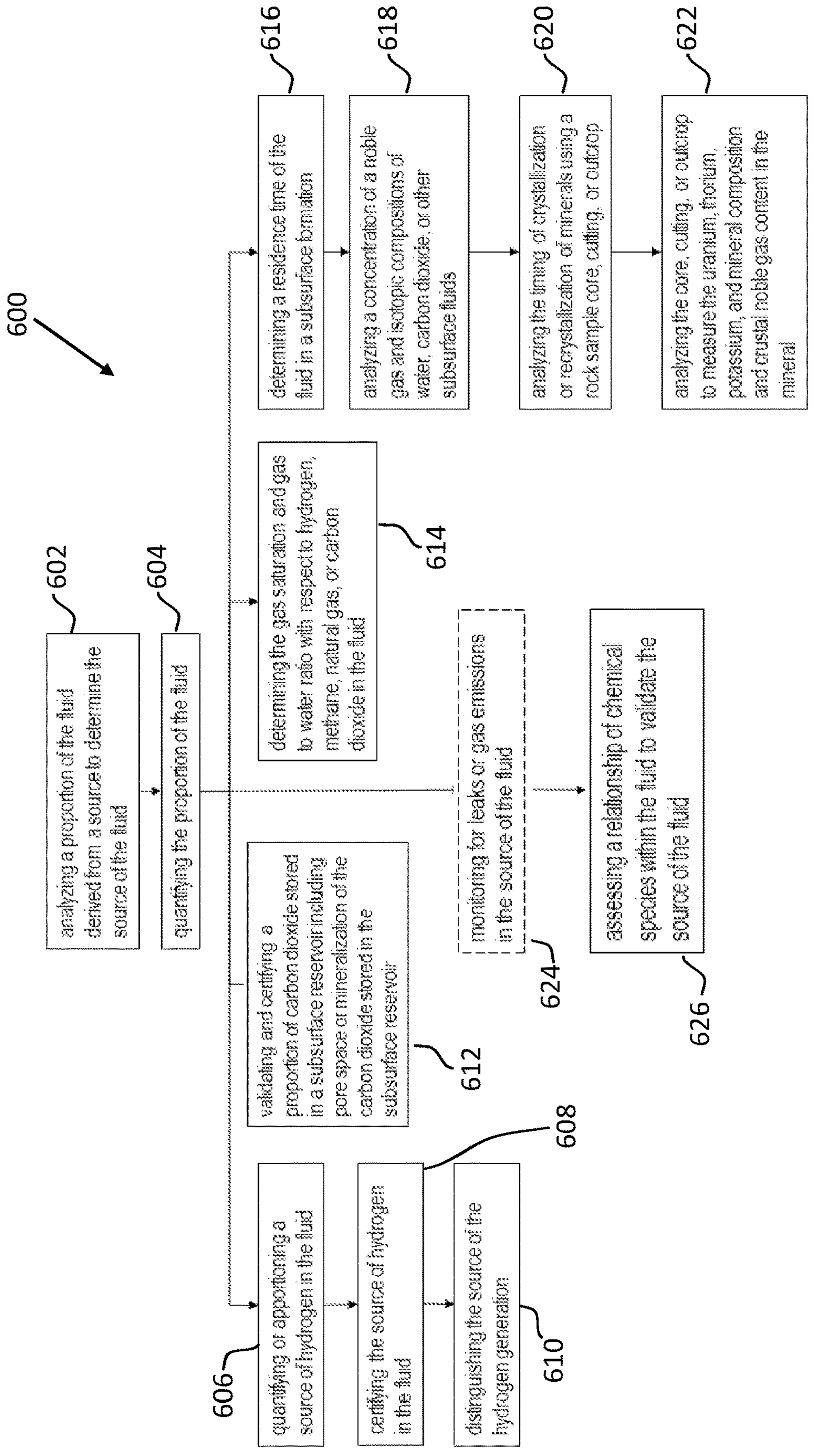
FIG. 6 is a flow chart of a method for assessing a molecular composition of a fluid, according to an embodiment.

FIG. 6 is a flow chart of a method 600 for assessing a molecular composition of a fluid, according to an embodiment. In some examples, the method 600 can include act 602 of analyzing a proportion of the fluid derived from a source to determine the source of the fluid. For example, the fluid comprises a gas or the mixture of gases including at least one of hydrogen, helium, a noble gas, ammonia, carbon dioxide, dihydrogen sulfide, nitrogen, or hydrocarbon gases. Hydrogen produced by various inorganic processes displays a predictable relationship with temperature and the original source of water from which hydrogen is derived. Other fluids can include similar unique signatures. Analyzing a proportion of the fluid derived from a source to determine the source of the fluid can include analyzing the fluid to determine one or more properties of the fluid or components therein, such as isotopic content. Any of the analytical techniques disclosed herein may be utilized to analyze the proportion of the fluid.

The method 600 can include the act 604 of quantifying the proportion of the fluid. Act 604 can include quantifying or apportioning the source of hydrogen in natural gas can include quantifying or apportioning the source of hydrogen. In other words, the fluid analysis can include an amount or percentage of the components of the fluid and expressing the amount or percentage as data. Quantifying the proportion of the fluid may include utilizing mixing algorithms or the like to determine the possible or likely ratio of component(s) in the fluid (e.g., types and amounts of isotopes, types and amounts of chemical species).

The method 600 can include act 606 of quantifying or apportioning a source of hydrogen in the fluid. The source can include at least one of natural gas pipelines, hydrogen pipelines, oil pipelines, water pipelines, railcars, trucks, industrial and storage facilities, springs, surface seeps, subsurface reservoir, or boreholes for oil, natural gas, water, or hydrogen wells. The quantifying and apportioning can assign a ratio, percentage, or other numerical value of the components (e.g., hydrogen or isotopes thereof) of the fluid and the source(s) associated therewith can be generated.

The method 600 can include act 608 of certifying the source of hydrogen in the fluid. Verification and certification can be determined by tracking of "green" hydrogen and derivative chemicals for which hydrogen is a feedstock. In some examples, certifying the source includes comparing the determined values for the source to one or more known values for natural hydrogen or new hydrogen sources. In some examples, the certifying of the source is done by comparison of the determined isotopic ratio of hydrogen to one or more known values for natural hydrogen or new hydrogen.

The method 600 can also include act 610 of distinguishing the source of the hydrogen generation. For example, by determining the residence time of the hydrogen (or other gases), the geological age (e.g., timing of) the hydrogen generation in a given subsurface formation can be used to distinguish among various potential sources of hydrogen. For example, natural hydrogen may be stored in a subsurface formation (in a gas, liquid, or mineral) for thousands to millions of years, while a newer hydrogen may be obtained from more modern sources. The hydrogen from the various sources has isotopic contents that are distinct from one another and indicative of the source of hydrogen generation. Accordingly, the determined residence time and associated source of hydrogen generation determined from the residence time can be used to evaluate the eligibility of the hydrogen for the United State Internal Revenue Service 45V production tax credit, various Low Carbon Fuel Standards, or other incentive, subsidy, or tax credit programs. The residence time may be determined by analyzing the isotopic content (e.g., ratio) of the hydrogen in the fluid.

The method 600 can include an act 612 of validating and certifying a proportion of carbon dioxide stored in a subsurface reservoir and the form of the storage including pore space or mineralization. For example, the carbon dioxide can be certified according to its source as a reaction product or as a stored and/or converted product based at least in part on the isotopic content of the carbon dioxide. In some examples, the carbon dioxide can be mineralized and sequestered, where the history and/or formation of the carbon dioxide is analyzed and validated for tax credit. Such validation or certification can include documenting the proportion of carbon dioxide stored in the subsurface reservoir, such as by attaching test results and data analysis to a certification statement.

The method 600 can include act 614 of determining the gas saturation and gas to water ratio with respect to hydrogen, methane, natural gas, or carbon dioxide in the fluid, wherein the fluids are collected at the surface or from a subsurface formation. Gas saturation can be defined as the percentage or fraction of adsorbed gas content relative to adsorption capacity. This value can be determined for a fluid sample at a given pressure and temperature by comparing desorption data with an adsorption isotherm derived from that sample. The saturation data can be an important characteristic parameter which determines at what saturation the trapped gas can be remobilized.

The method 600 can include act 616 of determining a residence time of the fluid in a subsurface formation. The residence time of a fluid is a determination of the time that the fluid has spent inside a volume. The residence time can provide insight and data into the type of fluid present in the volume. Determining the residence time can include act 618 of analyzing a concentration of a noble gas elemental (e.g., helium-4) and isotopic compositions of water, carbon dioxide, or other subsurface fluids. Determining the residence time can include an act 620 of analyzing the abundance of radiogenic gases in derived fluids or in minerals formed during water-rock interactions that generate hydrogen. These measurements can be performed in gases, formation water or other fluids, or by collecting and separating select minerals (e.g., magnetite, ilmenite) from a rock sample core, drill cuttings, or from an outcrop. For example, the timing of hydrogen generation in a subsurface formation can be derived by analyzing the core, cutting, or outcrop to measure the parent isotope (e.g., source of radioactivity) uranium (Uranium-238, Uranium-235), thorium (thorium 232), or potassium (potassium-40) abundance and the daughter isotope (e.g., helium-4, neon-21, argon-40) abundance in component minerals (e.g., magnetite source of hydrogen generation), as shown in act 622. Based on these measurements, the age or residence time of the fluid can be calculated using the formula, N(t)=N(0)e^−(λ*t), where N(t) is the number of atoms measured now, N(0) is the initial number of atoms as inferred by the measured abundance of daughter (or radiogenic) isotopes, X is the radioactive decay constant for a given parent isotope (or radioactive mineral), and t is residence time. By rearranging the formula to solve for t, the residence time can be calculated.

The method 600 can optionally include act 624 of monitoring for leaks or gas emissions in the least one of the sources. The methods and systems can apply to hydrogen from inputs and offtakes of natural gas in pipelines; inputs and offtakes of natural gas transported by other means. For example, prospective leaks or fugitive or stray natural gas investigations involving hydrogen can be monitored by either the systems described herein or independent monitoring systems. In some examples, the hydrogen leaks and/or gas emissions can be monitored for gas losses and for safety purposes.

The method 600 can include the act 626 of assessing the relationships of chemical species within the fluid to validate the source of the fluid. The proportions of components of the fluid can be determined to measure and confirm the source of a fluid, specifically a fluid that includes a mixture of components. Such validation may include comparisons to statistical data of chemical species, mixtures, or the like for known sources to the determined statistical data of the fluid. For example, matching statistical data of the chemical species, mixture, or the like for a known source and the fluid can validate the source of the fluid. A fluid mixture from a selected source may have proportions of components that have unique statistical data that does not correlate to other mixtures or fluid sources. Accordingly, a match between statistical data (e.g., proportions of components, residence time, isotopic content, or the like) for a known source can be used to identify an unknown source of a fluid sample.

One or more portions of the method 600 can be carried out using any of the techniques disclosed herein. For example, the method 600 may be carried out using the techniques disclosed with respect to the method 300 or the method 700. Likewise, portions of the method 700 below may be carried out using any portions of the methods and techniques disclosed herein.

Figure 7:
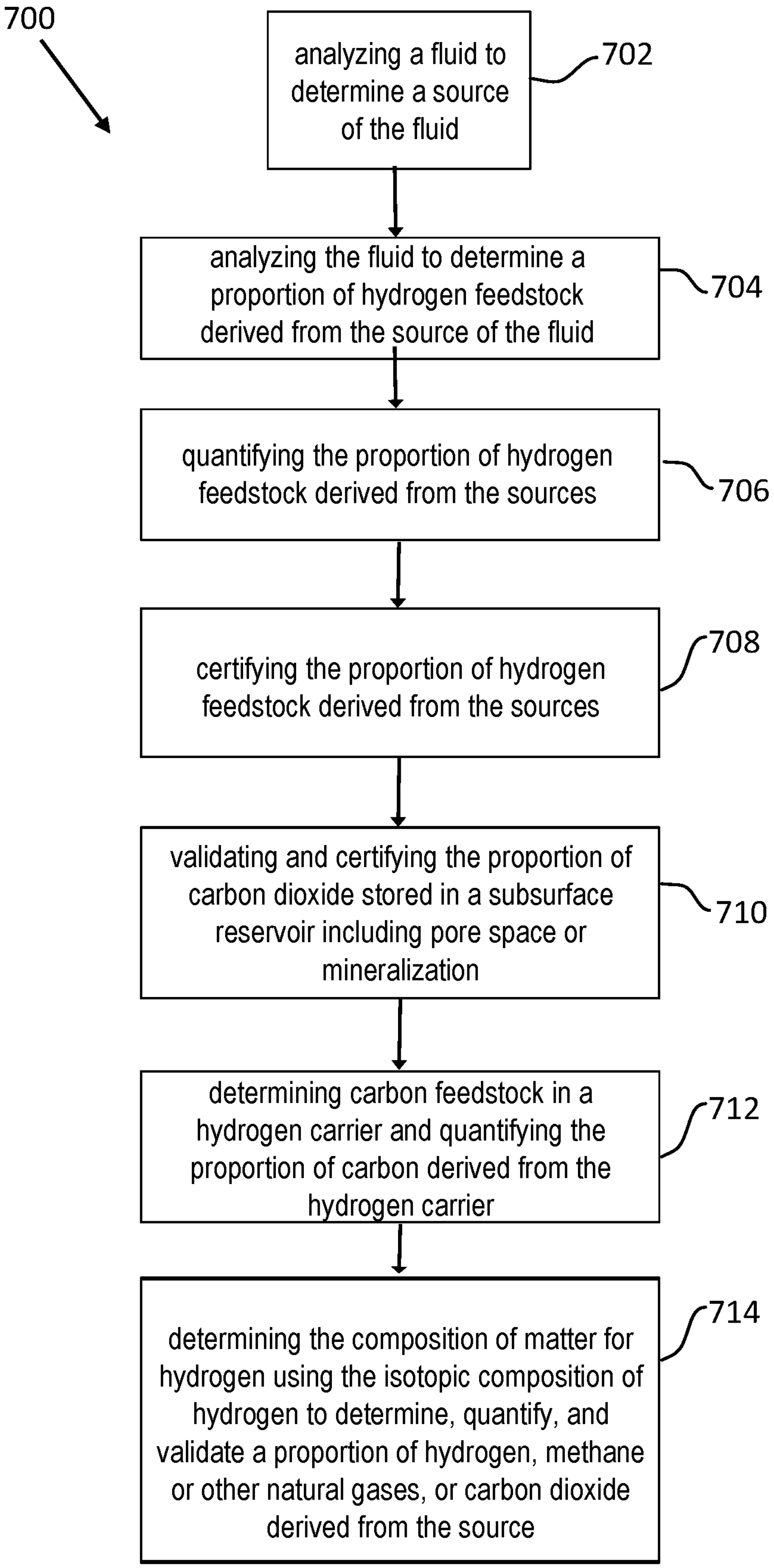
FIG. 7 is a flow chart of a method for analyzing an isotopic composition, according to an embodiment.

FIG. 7 is a flow chart of a method 700 for analyzing an isotopic composition. Analyzing the isotopic composition can be utilized to determine characteristics of hydrogen incorporated into newer chemical species, such as fuels, ammonia, petroleum, polymers or the like. In some examples, the method 700 can include the act 702 of analyzing an isotopic composition of a fluid to determine a source of the fluid. The isotopic composition may include the isotopic value of hydrogen (e.g., $\delta^2H—H_2$) or other molecules, such as helium, methane, ethane. The analysis can include using any of the analytical techniques and systems described herein. The fluids can include at least one of hydrogen, helium, ammonia, carbon dioxide, dihydrogen sulfide, nitrogen, methane or hydrocarbon gas, water, methanol, synthetic fuels, ammonia, or carbon dioxide. In some examples, the source can include at least one of a geologic hydrogen, coal, natural gas, biomass, ammonia, steel manufacturing, synthesis of chemicals, waste incineration, gas processing, atmospheric capture, natural gas pipelines, hydrogen pipelines, oil pipelines, water pipelines, railcars, trucks, steam methane reformation, pyrolysis, chemical looping, or electrolysis.

The method 700 can include an act 704 of analyzing the fluid to determine a proportion of hydrogen feedstock derived from the source of the fluid. For example, derivative products for which hydrogen is a feedstock can include at least one of ammonia, methanol, hydrogen-derived synthetic/electrofuels, such as renewable or low-carbon kerosene, diesel, jet fuel, plastics, synthetic methane, or other hydrogen carriers or products; other hydrogen carriers; or synthetic plastics. Hydrogen derived from these sources can have characteristic properties not associated with other sources, such as natural hydrogen stored in subsurface rock formations. In some examples, the source and proportion of various hydrogen supplies can be determined and verification of low-carbon hydrogen status. In some examples, analyzing the fluid includes comparing a measurement of an isotopic ratio of hydrogen from a sample with data for isotopic ratios of hydrogen for known samples of hydrogen (e.g., natural hydrogen; or electrolytic hydrogen, hydrogen from pyrolysis, or other new forms of hydrogen).

The method 700 can include an act 706 of quantifying the proportion of hydrogen feedstock derived from the sources. Quantifying the proportion of hydrogen feedstock derived from the sources can include quantifying how much hydrogen incorporated into newly formed chemical species (e.g., ammonia, synthetic fuels, petroleum) is derived from the sources. Such quantification can include determining the proportion from the isotopic composition of the hydrogen (or other atoms) in the newer chemical and comparing the same to known isotopic composition data for the newer chemical made with natural hydrogen or new forms of hydrogen.

The method 700 can include an act 708 of certifying the proportion of hydrogen feedstock derived from the sources. For example, certifying the source of hydrogen can include certifying the source in at least one of a natural gas pipeline, hydrogen pipeline, oil pipeline, water pipeline, railcar, truck, or industrial facility. Certifying the source can include documenting (e.g., correlating or storing) the analyses (and finding thereof) used to determine the source(s) and proportion(s) of the hydrogen in the fluid.

In some examples, the method 700 can include validating and certifying the proportion of carbon dioxide stored in a subsurface reservoir including pore space or mineralization. For example, the carbon dioxide can be certified according to its source as a reaction product or as a stored and/or converted product. In some examples, the carbon dioxide can be mineralized and sequestered, where the history and/or formation of the carbon dioxide is analyzed and validated for tax credit. Such validation and certification may include documenting the findings of the analyses corresponding the fluid and source thereof, such as providing a statement or certification form to a record keeping entity, governmental organization, hydrogen user, or hydrogen supplier.

In some examples, the method 700 can include an act 712 that includes determining carbon feedstock in a hydrogen carrier and quantifying the proportion of carbon derived from the hydrogen carrier. In some examples, the hydrogen carrier can include at least one of coal combustion, natural gas combustion, biomass incineration, ammonia syntheses, steel manufacturing, chemical synthesis, waste incineration, and atmospheric capture.

In some examples, the method 700 can include and act 714 of determining the composition of matter for hydrogen using the isotopic composition of hydrogen to determine, quantify, and validate a proportion of hydrogen, methane or other natural gases, or carbon dioxide derived from the source. As such, the method 700 can be conducted by using chemical instruments to measure elements, molecules, isotopes, or isotopic ratios by visual inspection, quantitative analysis, or supervised or unsupervised computer-assisted machine learning enable the identification and characterization of the source of hydrogen or carbon dioxide in the subsurface or various chemicals, in chemical feedstocks, in products derived using hydrogen as a feedstock, or other energy sources at the surface and also in a subsurface formation.

In some examples, a method for analyzing a molecular composition can include analyzing hydrogen molecules, hydrocarbon gases, noble gases, carbon dioxide, nitrogen, and mixtures of natural gases of varying composition to determine the source of hydrogen, carbon dioxide, or natural gas. In some examples, a method for analyzing the molecular composition of hydrogen and other gas mixtures can include assessing a proportion of hydrogen derived from sources including geologic hydrogen, coal, steam methane reformation, pyrolysis, chemical looping, or electrolysis sources, quantifying the proportion of hydrogen derived from the sources, and validating and certifying the proportion of hydrogen derived from no-carbon, low-carbon, and/or high-carbon sources including geologic hydrogen, coal, steam methane reformation, pyrolysis, chemical looping, or electrolysis sources.

In some examples, a method for analyzing an isotopic composition can include analyzing at least one of hydrogen molecules, hydrocarbon gases, noble gases, carbon dioxide, nitrogen, or mixtures of natural gases of varying composition to determine the source of hydrogen, carbon dioxide, or natural gas, analyzing water to determine a feedstock for hydrogen formation by electrolysis of the water, and analyzing methane or other hydrocarbon gases to determine a feedstock for hydrogen formation by pyrolysis, steam methane reforming, or steam methane reforming combined with carbon capture utilization and storage of methane or other hydrocarbon gas feedstocks.

In some examples, a method for analyzing an isotopic composition can include assessing a proportion of hydrogen, carbon dioxide, or natural gas derived from sources including one or more of geologic hydrogen, coal, steam methane reformation, pyrolysis, chemical looping, or electrolysis, quantifying the proportion of hydrogen or carbon dioxide derived from the sources, and validating and certifying the proportion of hydrogen derived from no-carbon, low-carbon, and/or high-carbon sources including geologic hydrogen, coal, steam methane reformation, pyrolysis, chemical looping, or electrolysis.

In some examples, a method for analyzing the isotopic composition of hydrogen in ammonia can include determining the source of hydrogen feedstocks used in ammonia production; determining the proportion of hydrogen feedstock derived from sources including geologic hydrogen, coal, steam methane reformation, pyrolysis, chemical looping, or electrolysis; quantifying the proportion of hydrogen feedstock derived from the sources; and certifying the proportion of hydrogen feedstock derived from the sources.

In some examples, a method for analyzing the isotopic composition of hydrogen and carbon in methanol can include determining a source of hydrogen or carbon feedstocks used in methanol production; determining a proportion of hydrogen derived from sources including at least one of geologic hydrogen, coal, steam methane reformation, pyrolysis, chemical looping, or electrolysis; determining the proportion of carbon derived from sources including at least one of coal combustion, natural gas combustion, biomass incineration, ammonia synthesis, steel manufacturing, synthesis of lime and other chemicals, waste incineration, gas processing, atmospheric capture, or other forms; quantifying the proportion of hydrogen feedstock or carbon derived from the sources including one or more of geologic hydrogen, coal, steam methane reformation, pyrolysis, chemical looping, or electrolysis; certifying the proportion of hydrogen feedstock and carbon derived from the sources including one or more of geologic hydrogen, coal, steam methane reformation, pyrolysis, chemical looping, or electrolysis; and certifying the proportion of carbon derived from the sources including one or more of coal combustion, natural gas combustion, biomass incineration, ammonia synthesis, steel manufacturing, synthesis of lime and other chemicals, waste incineration, gas processing, atmospheric capture, or other forms.

In some examples, a method for analyzing the isotopic composition of hydrogen and carbon in synthetic/electrofuels, such as renewable or low-carbon kerosene, diesel, jet fuel, plastics, synthetic methane, or other hydrogen carriers can include determining the source of hydrogen and carbon feedstocks in synthetic/electrofuels, such as renewable or low-carbon kerosene, diesel, jet fuel, plastics, synthetic methane, or other hydrogen carriers; quantifying the proportion of hydrogen derived from sources including one or more of geologic hydrogen, coal, steam methane reformation, pyrolysis, chemical looping, or electrolysis sources in synthetic/electrofuels; quantifying the proportion of carbon derived from sources including one or more of coal combustion, natural gas combustion, biomass incineration, ammonia synthesis, steel manufacturing, synthesis of lime and other chemicals, waste incineration, gas processing, atmospheric capture, or other forms in electrofuels; certifying the proportion of hydrogen derived from the sources including one or more of geologic hydrogen, coal, steam methane reformation, pyrolysis, chemical looping, or electrolysis sources in electrofuels; and certifying the proportion of carbon derived from the sources including one or more of coal combustion, natural gas combustion, biomass incineration, ammonia synthesis, steel manufacturing, synthesis of lime and other chemicals, waste incineration, gas processing, atmospheric capture, or other forms in electrofuels.

In some examples, a method for analyzing the isotopic composition of hydrogen and carbon in hydrogen carriers can include determining sources of hydrogen and carbon feedstocks in hydrogen carriers; quantifying the proportion of hydrogen derived from sources including at least one of geologic hydrogen, coal, steam methane reformation, pyrolysis, chemical looping, or electrolysis sources in hydrogen carriers; quantifying the proportion of carbon derived from sources including at least one of coal combustion, natural gas combustion, biomass incineration, ammonia synthesis, steel manufacturing, synthesis of lime and other chemicals, waste incineration, gas processing, atmospheric capture, or other forms in hydrogen carriers; certifying the proportion of hydrogen derived from the sources including at least one of geologic hydrogen, coal, steam methane reformation, pyrolysis, chemical looping, or electrolysis sources in hydrogen carriers; and certifying the proportion of carbon derived from the sources including at least one of coal combustion, natural gas combustion, biomass incineration, ammonia synthesis, steel manufacturing, synthesis of lime and other chemicals, waste incineration, gas processing, atmospheric capture, or other forms in hydrogen carriers.

In some examples, a method for determining the source of hydrogen in natural gas can include determining the source of hydrogen in at least one of natural gas pipelines, hydrogen pipelines, oil pipelines, water pipelines, railcars, trucks, or industrial facilities. The method can include comparing a measurement of an isotopic ratio of hydrogen from a sample with data for isotopic ratios of hydrogen for known samples of hydrogen.

In some examples, a method for quantifying or apportioning the source of hydrogen in natural gas can include quantifying or apportioning the source of hydrogen in at least one of natural gas pipelines, hydrogen pipelines, oil pipelines, water pipelines, railcars, trucks, or industrial facilities.

In some examples, a method for certifying the source of hydrogen in natural gas for a US IRS 45V production tax credit, Low Carbon Fuel Standards, or other hydrogen incentive, subsidy, or credit programs can include certifying the source of hydrogen in at least one of natural gas pipelines, hydrogen pipelines, oil pipelines, water pipelines, railcars, trucks, or industrial facilities.

In some examples, a method for determining a source of hydrogen can include determining the source of hydrogen in fluids collected at the surface or from the subsurface for the purposes of exploration of oil, natural gas, hydrogen, carbon dioxide, helium, or other gases; determining the source of hydrogen in fluids collected at the surface or from the subsurface for the purposes of drilling, including measurement while drilling, drill-stem test, or pressure-volume-temperature (PVT) operations, for oil, natural gas, hydrogen, carbon dioxide, helium, or other gases; determining the source of hydrogen in fluids collected at the surface or from the subsurface for the purposes of production of oil, natural gas, hydrogen, carbon dioxide, helium, or other gases; determining the source of hydrogen in fluids collected at the surface or from the subsurface for the purposes of monitoring and evaluation of the storage of oil, natural gas, hydrogen, carbon dioxide, helium, or other gases in subsurface reservoirs; determining the source of hydrogen in fluids collected at the surface or the subsurface for the purposes of monitoring and evaluation of the storage of oil, natural gas, hydrogen, carbon dioxide, helium, or other gases in subsurface caverns; determining the source of hydrogen in fluids collected at the surface or the subsurface for the purposes of monitoring and evaluation of the storage of oil, natural gas, hydrogen, carbon dioxide, helium, or other gases in surface tanks, subsurface tanks, or other industrial facilities; and determining the source of hydrogen in fluids collected at the surface or from the subsurface for the purposes of monitoring and evaluation the presence of leaks or fugitive, stray, or other gas emissions in boreholes, oil, natural gas, or hydrogen wells, pipelines, water wells, surface seeps, springs, or other storage facilities.

In some examples, a method for determining the composition of matter for hydrogen using the isotopic composition of hydrogen can include using the isotopic composition of hydrogen of at least one of ammonia, methanol, synthetic or electrofuels, plastics, various other green hydrogen sources, various other chemicals where hydrogen is used as a feedstock, fluids collected at surface regions including springs and surface seeps or from the subsurface for the purposes of monitoring and evaluation of the storage of oil, natural gas, or hydrogen in surface tanks, subsurface tanks, or other industrial facilities, or fluids collected at the surface regions or from the subsurface for the purposes of monitoring and evaluation the presence of leaks or fugitive, stray, or other gas emissions in boreholes, oil, natural gas, or hydrogen wells, pipelines, water wells, surface seeps, springs, or other storage facilities.

The analytical techniques for determining isotopic compositions, sources, proportions, etc. of hydrogen, carbon, or other chemical components disclosed herein may be used for any of the methods disclosed herein.

In the production of natural resources from formations within the earth, a well or borehole is drilled into the earth to the location where the natural resource is believed to be located. Similarly in the sequestration of greenhouse gases or other waste products in formations within the earth, a well or borehole is drilled into the earth to the location where the greenhouse gas or other waste product will be injected, stored, and sequestered. These natural resources may be hydrogen; helium; carbon dioxide; dihydrogen sulfide; methane or other hydrocarbon gases; a dihydrogen sulfide reservoir; a hydrogen reservoir; a helium reservoir; a carbon dioxide reservoir; a natural gas reservoir; a reservoir rich in dihydrogen sulfide; a reservoir rich in hydrocarbons; a reservoir rich in helium; the natural resource may be fresh water; brackish water; brine; it may be a heat source for geothermal energy; or it may be some other natural resource, ore deposit, mineral, metal, or gem that is located within the ground.

These resource-containing formations may be a few hundred feet, a few thousand feet, or tens of thousands of feet below the surface of the earth, including under the floor of a body of water, e.g., below the seafloor or beneath other natural resources, e.g., below aquifers. These formations may also cover areas of differing sizes, shapes, and volumes.

Typically, and by way of general illustration, in drilling a well an initial borehole is made into the earth, e.g., the surface of land or seabed, then subsequent smaller diameter boreholes are drilled to extend the overall depth of the borehole. In this manner as the overall borehole gets deeper its diameter becomes smaller; resulting in what can be envisioned as a telescoping assembly of holes with the largest diameter hole at the top of the borehole closest to the surface of the earth.

Thus, by way of example, the starting phases of a subsea drill process may be explained in general as follows. Once the drilling rig is positioned on the surface of the water over the area where drilling is to take place, an initial borehole is made by drilling a 36" hole in the earth to a depth of about 200-300 ft. below the seafloor. A 30" casing is inserted into this initial borehole. This 30" casing may also be called a conductor. The 30" conductor may or may not be cemented into place. During this drilling operation a riser is generally not used and the cuttings from the borehole, e.g., the earth and other material removed from the borehole by the drilling activity are returned to the seafloor. Next, a 26" diameter borehole is drilled within the 30" casing, extending the depth of the borehole to about 1,000-1,500 ft. This drilling operation may also be conducted without using a riser. A 20" casing is then inserted into the 30" conductor and 26" borehole. This 20" casing is cemented into place. The 20" casing has a wellhead secured to it. (In other operations an additional smaller diameter borehole may be drilled, and a smaller diameter casing inserted into that borehole with the wellhead being secured to that smaller diameter casing.) A BOP (blow out preventer) is then secured to a riser and lowered by the riser to the seafloor, where the BOP is secured to the wellhead. From this point forward all drilling activity in the borehole takes place through the riser and the BOP.

It should be noted that riserless subsea drilling operations are also contemplated.

For a land-based drill process, the steps are similar, although the large diameter tubulars, 30"-20" are typically not used. Thus, and generally, there is a surface casing that is typically about 13⅜" diameter. This may extend from the surface, e.g., wellhead and BOP, to depths of tens of feet to hundreds of feet. One of the purposes of the surface casing is to meet environmental concerns in protecting groundwater by preventing surface casing ventflow to groundwater aquifers or prevent surface casing ventflow of greenhouse gases or flammable gases to groundwater aquifers or the atmosphere. The surface casing should have sufficiently large diameter to allow the drill string, production equipment such as electronic submersible pumps (ESPs) and circulation mud to pass through. Below the casing one or more different diameter intermediate casings may be used. (It is understood that sections of a borehole may not be cased, which are referred to as open hole.) These can have diameters in the range of about 9" to about 7", although larger and smaller sizes may be used, and can extend to depths of thousands to tens of thousands of feet. The section of the well located within the reservoir, such as the section of the formation containing the natural resources, can be called the pay zone. Inside of the casing and extending from a pay zone, or production zone of the borehole up to and through the wellhead on the surface is the production tubing. There may be a single production tubing or multiple production tubings in a single borehole, with each of the production tubing endings at different depths.

Fluid communication between the formation and the well can be greatly increased by the use of hydraulic fracturing or other stimulation techniques. The first uses of hydraulic fracturing date back to the late 1940s and early 1950s. In general, hydraulic fracturing treatments involve forcing fluids down the well and into the formation, where the fluids enter the formation and crack, e.g., force the layers of rock to break apart or fracture. These fractures create channels or flow paths that may have cross sections of a few microns, to a few millimeters, to several millimeters in size, and potentially larger. The fractures may also extend out from the well in all directions for a few feet, several feet, and tens of feet or further. The fractures may be kept open by using a proppant (e.g., various sized sand or other mineral grains) that is forced down the well with the fracturing fluid in a single operation. It should be remembered that the longitudinal axis of the well in the reservoir may not be vertical: it may be on an angle (either sloping up or down) or it may be horizontal.

As used herein, unless specified otherwise, the terms “hydrogen exploration and production,” “carbon dioxide exploration and production,” “helium exploration and production,” “dihydrogen sulfide exploration and production,” “exploration and production activities,” “E&P,” “E&P activities,” and similar such terms are to be given their broadest possible meaning, and include surveying, geological analysis, chemical assessment, well planning, reservoir planning, reservoir management, drilling a well, workover and completion activities, hydrogen production, flowing of hydrogen from a well, collection of hydrogen, secondary and tertiary recovery from a well, the management of flowing hydrogen from a well, carbon dioxide injection, carbon dioxide sequestration, carbon dioxide mineralization, dihydrogen sulfide injection, dihydrogen sulfide sequestration, dihydrogen sulfide mineralization, and any other upstream activities.

As used herein, unless specified otherwise, the terms “sulfur mineralization,” “sulfur sequestration,” “sulfur mitigation,” “carbon dioxide mineralization,” “carbon dioxide sequestration,” “carbon dioxide mitigation,” “carbon mineralization,” “carbon sequestration,” “carbon mitigation,” and similar such terms are to be given their broadest possible meaning, and include surveying, geological analysis, well planning, reservoir planning, reservoir management, drilling a well, workover and completion activities, sulfur injection, dihydrogen sulfide injection, carbon injection, carbon dioxide injection, the management of flowing sulfur, dihydrogen sulfide, carbon, carbon dioxide to a well, and any other upstream activities.

As used herein, unless specified otherwise, the term “earth” should be given its broadest possible meaning, and includes the ground, all natural materials, such as rocks, and artificial materials, such as concrete, borehole casing, piping, or fill, that are or may be found in the ground.

As used herein, unless specified otherwise “offshore” and “offshore drilling activities” and similar such terms are used in their broadest sense and would include drilling activities on, or in, any body of water, whether fresh or salt water, whether manmade or naturally occurring, such as for example rivers, lakes, canals, inland seas, oceans, seas, such as the North Sea, bays and gulfs, such as the Gulf of Mexico. As used herein, unless specified otherwise the term “offshore drilling rig” is to be given its broadest possible meaning and would include fixed towers, tenders, platforms, barges, jack-ups, floating platforms, drill ships, dynamically positioned drill ships, semi-submersibles and dynamically positioned semi-submersibles. As used herein, unless specified otherwise the term “seafloor” is to be given its broadest possible meaning and would include any surface of the earth that lies under, or is at the bottom of, any body of water, whether fresh or salt water, whether manmade or naturally occurring.

As used herein, unless specified otherwise, the term “borehole” should be given its broadest possible meaning and includes any opening that is created in the earth that is substantially longer than it is wide, such as a well, a well bore, a well hole, a micro hole, a slimhole and other terms commonly used or known in the arts to define these types of narrow long passages. Wells would further include exploratory, discovery, production, abandoned, reentered, reworked, recirculation, and injection wells. They would include both cased and uncased wells, and sections of those wells. Uncased wells, or section of wells, also are called open holes, boreholes, open boreholes, open bores, or open hole sections. Boreholes may further have segments or sections that have different orientations, they may have straight sections and arcuate sections and combinations thereof. Thus, as used herein unless expressly provided otherwise, the “bottom” of a borehole, the “bottom surface” of the borehole and similar terms refer to the end of the borehole or that portion of the borehole furthest along the path of the borehole from the borehole’s opening, the surface of the earth, or the borehole’s beginning. The terms “side” and “wall” of a borehole should be given their broadest possible meaning and include the longitudinal surfaces of the borehole, whether or not casing or a liner is present; as such, these terms would include the sides of an open borehole or the sides of the casing that has been positioned within a borehole. Boreholes may be made up of a single passage, multiple passages, connected passages, (e.g., branched configuration, fishboned configuration, dual-lateral configuration, trilateral configuration, quadrilateral configuration, pitchfork configuration, pinnate configuration, or comb configuration), and combinations and variations thereof.

Boreholes are generally formed and advanced by using mechanical drilling equipment having a rotating drilling tool, e.g., a bit. For example, and in general, when creating a borehole in the earth, a drilling bit is extending to and into the earth and rotated to create a hole in the earth. To perform the drilling operation the bit must be forced against the material to be removed with a sufficient force to exceed the shear strength, compressive strength, or combinations thereof, of that material. The material that is cut from the earth is generally known as cuttings or drill cuttings, e.g., waste, which may be chips of rock, dust, rock fibers, and other types of materials and structures that may be created by the bit's interactions with the earth. These cuttings are typically removed from the borehole by the use of fluids, which fluids can be liquids, foams, or gases, or other materials known to the art.

As used herein, unless specified otherwise, the term "drill pipe" is to be given its broadest possible meaning and includes all forms of pipe used for drilling activities; and refers to a single section or piece of pipe. As used herein the terms "stand of drill pipe," "drill pipe stand," "stand of pipe," "stand" and similar type terms should be given their broadest possible meaning and include two, three, or four sections of drill pipe that have been connected, e.g., joined together, typically by joints having threaded connections. As used herein the terms "drill string," "string," "string of drill pipe," "string of pipe," and similar type terms should be given their broadest definition and would include a stand or stands joined together for the purpose of being employed in a borehole. Thus, a drill string could include many stands and many hundreds of sections of drill pipe.

As used herein, unless specified otherwise, the terms "formation," "reservoir," "pay zone," and similar terms, are to be given their broadest possible meanings and would include all locations, areas, and geological features within the earth that contain, may contain, or are believed to contain, hydrogen, carbon dioxide, helium, dihydrogen sulfide, or natural gas.

As used herein, unless specified otherwise, the terms "field," "oil field," "gas field" and similar terms, are to be given their broadest possible meanings, and would include any area of land, seafloor, or water that is loosely or directly associated with a geologic formation, and more particularly with a resource containing formation, thus, a field may have one or more exploratory and producing wells associated with it, a field may have one or more governmental body or private resource leases associated with it, and one or more field(s) may be directly associated with a resource containing formation.

As used herein, unless specified otherwise, the terms "conventional hydrogen," "conventional carbon dioxide," "conventional helium," "conventional dihydrogen sulfide," "conventional natural gas," "conventional," "conventional production" and similar such terms are to be given their broadest possible meaning and include hydrogen, carbon dioxide, helium, or dihydrogen sulfide that are trapped in structures in the earth. Generally, in these conventional formations, the hydrogen, carbon dioxide, helium, dihydrogen sulfide, or natural gas have migrated in permeable or semi-permeable formations to a trap or area where they are accumulated. Typically, in conventional formations, a non-porous, relatively impermeable layer is above, or encompassing the area of accumulated hydrogen, carbon dioxide, helium, dihydrogen sulfide, or natural gas, in essence trapping the hydrogen, carbon dioxide, helium, dihydrogen sulfide, or natural gas in the accumulation. Conventional reservoirs have been historically the sources of the vast majority of natural gas, hydrogen, carbon dioxide, helium, and dihydrogen sulfide observed. As used herein, unless specified otherwise, the terms "unconventional hydrogen," "unconventional carbon dioxide," "unconventional helium," "unconventional dihydrogen sulfide," "unconventional natural gas," "unconventional," "unconventional production," and similar such terms are to be given their broadest possible meaning and includes hydrogen, carbon dioxide, helium, dihydrogen sulfide, or natural gas that are held in impermeable rock, or which have not migrated to traps or areas of accumulation.

As used herein, unless specifically stated otherwise, the term "gold hydrogen" should be given its broadest possible meaning, and generally refers to hydrogen produced from the subsurface by drilling into and recovering hydrogen from subsurface systems or stimulating iron-rich rock, mafic rock, pyrite, iron-rich sandstone, iron-rich sediments, uranium- and thorium-rich rock, or uranium- and thorium-rich sediments with or without fracturing or other forms of mechanical stimulation that can provide an abundant source of low emission, low cost, fully dispatchable energy.

As used herein, unless specifically stated otherwise, the term "molecule" should be given its broadest possible meaning, and generally refers to a group of atoms bonded together, representing the smallest fundamental unit of a chemical compound that can take part in a chemical reaction.

As used herein, unless stated otherwise, room temperature is 25° C. And, standard temperature and pressure is 25° C. and 1 atmosphere.

Generally, the term "about" as used herein unless specified otherwise is meant to encompass a variance or range of +10%, the experimental or instrument error associated with obtaining the stated value, and preferably the larger of these.

As used herein unless specified otherwise, the recitation of ranges of values herein is merely intended to serve as a shorthand method of referring individually to each separate value falling within the range. Unless otherwise indicated herein, each individual value within a range is incorporated into the specification as if it were individually recited herein.

The term "$CO_2$e" is used to define carbon dioxide equivalence of other, more potent greenhouse gases, to carbon dioxide (e.g., methane and nitrous oxide) on a global warming potential basis of 100 years, based on IPCC AR5 methodology. The term "carbon intensity" is taken to mean the lifecycle $CO_2$e generated per unit mass of a product.

$CO_2$ is widely recognized as a greenhouse gas (GHG), and the continued accumulation of $CO_2$ and other GHGs in the atmosphere is expected to cause problematic changes to global ecosystems and contribute to myriad other problems, such as ocean acidification and sea level rise. The two primary causes of carbon emissions globally are the use of fossil fuels for power generation and transportation.

Given the risks of $CO_2$ emissions, significant work has gone into finding replacements to existing high carbon energy sources, or ways to decarbonize existing energy sources. However, many of these low carbon alternatives have been uneconomic or not dispatchable enough to replace the current options.

The term "sulfur equivalents" of "SOX" is used to define dihydrogen sulfide or sulfur dioxide offset equivalence of sulfur emissions. The term "sulfur intensity" is taken to mean the lifecycle SOX generated per unit mass of a product.

Sulfur, in various forms, including but not limited to dihydrogen sulfide, sulfur dioxide, sulfuric acid, and sulfate, is widely recognized as a toxic and harmful atmospheric pollutant and the deposition of sulfur in soil, waterways, and other environments is expected to cause problematic changes to global ecosystems and contribute to myriad of other problems, such as acid rain, soil acidification, deforestation, ocean acidification, and other toxic impacts. The primary causes of dihydrogen sulfide emissions globally are related to petroleum and natural gas extraction and refining, pulp and paper manufacturing, rayon textile production, waste disposal, landfills, water and sewage treatment facilities, and general waste disposal. Additionally, natural factors such as volcanoes, hot springs, thermal vents, geysers, fumaroles, "sour" natural gas fields, biodegraded oil fields, or geothermal power plants also constitute major naturally occurring sources of dihydrogen sulfide.

Given the risks of dihydrogen sulfide and other forms of sulfur emissions, significant work has gone into sulfur removal technologies, the development of low sulfur fuels, or ways to desulfurize existing energy sources and processes. However, many of these low sulfur alternatives themselves create cost prohibitions, are uneconomic, or limit the dispatchability of energy sources.

Based on the risks of sulfur emissions, the U.S. EPA (IRC 45H) has created a cap-and-trade sulfur credit program for offset, sulfur abatement, and sequestration. The U.S. IRS 45Q tax credit program is a similar tax credit program for carbon dioxide sequestration.

In power generation, the alternatives to the highly reliable, low cost, but high emission sources (e.g., gas and coal) are either dispatchable and expensive (e.g., nuclear, hydroelectric, green hydrogen, or blue hydrogen), or inexpensive and intermittent (e.g., solar and wind, green hydrogen in some cases). There is only one existing source that is both lower cost and dispatchable, and that is geothermal. However, geothermal resources are limited, many of the economically productive geothermal resources have already been developed and are nearing end of life, and many geothermal resources are already in decline. As such, the growth outlook for geothermal energy resources is limited without significant technical advances.

Green hydrogen (hydrogen produced from water without the utilization of fossil fuels), which is generated by electrolysis powered from either solar, wind, hydroelectric, renewable natural gas combustion, or geothermal energy can be a reliable source of low carbon energy when coupled with storage, but high capital cost, intermittent production due to intermittent energy sources or high cost of energy when grid connected, and the high cost and low availability of suitable hydrogen storage resources limits applicability. In addition, electrolysis consumes significantly more energy to produce hydrogen than what is stored in the hydrogen, resulting in a low round trip efficiency in the system.

Blue hydrogen faces a similar set of problems to green hydrogen: it takes a low cost, high emission fuel source like coal or natural gas, and by adding expensive and parasitic carbon capture facilities, converts this low-cost-high-emission source of energy into a high-cost-low-emission source. Thus, even though large volumes of hydrogen can be formed in processes that subsequently prevent greenhouse gas emissions from reaching the atmosphere, the newly developed hydrogen resource is not cost competitive with other forms of energy derived from fossil fuels. Additionally, the challenges around finding carbon sequestration resources that can be used to permanently store the captured carbon from these processes result in limited opportunities to deploy these technologies today.

Natural hydrogen (or "gold hydrogen"), produced from the subsurface by drilling and stimulating iron-rich rock, mafic rock, pyrite, iron-rich sandstone, iron-rich sediments, uranium- and thorium-rich rock, uranium- and thorium-rich sediments with or without fracturing or other forms of mechanical stimulation can provide an abundant source of low emission, low cost, fully dispatchable energy.

Each of these energy sources and their inherent advantages and limitations are also relevant to transportation. When considering transportation fuels, by far the major sources of fuel are diesel and gasoline, both derived from crude oil production. Additionally, in recent years, electric vehicles have been gaining market share, but the cost for electric vehicles is still more expensive than fossil fueled equivalents and limitations exist regarding cost, recharge time, and primary resources for battery and energy storage. Given the weight of batteries, electric long-haul trucking is also challenging, and most long-haul truck manufacturers are in search of affordable, low carbon options such as hydrogen-fueled trucking.

Natural hydrogen produced by enhanced hydrogen production reactions would be an answer to the low or negative carbon, low cost, reliable transportation problem for long-haul trucking and potentially other forms of transportation. As for other types of transportation, natural hydrogen as a compressed or liquified product, or as a feedstock for synthetic liquid fuel ("efuels") would be a reliable low cost, low or negative-carbon solution. Additionally, natural hydrogen could be combined with nitrogen to produce a carbon free ammonia product, which is being widely discussed as a potential replacement for bunker fuel for shipping and as a feedstock for synthetic fertilizer manufacturing.

Direct Emissions Reduction: because there are no direct $CO_2$ emissions from the combustion or typical use of hydrogen, the reduction in $CO_2$ emissions is a function of what the hydrogen is replacing. In many cases, low carbon (or negative carbon) hydrogen would be replacing hydrogen from steam methane reforming (SMR) as a chemical feedstock for ammonia production, oil refining, and other chemical manufacturing. In some cases, low carbon (or negative carbon) hydrogen may replace natural gas, diesel fuel, gasoline, or jet fuel as a heat source or transportation fuel.

In the case of ammonia production and refining, natural gas is used to produce hydrogen via steam methane reformation reactions, which is used as a chemical feedstock in both the refining process and the ammonia production process. Today, more than 95‰ f hydrogen is produced using natural gas in steam methane reformers (SMRs). The carbon intensity of hydrogen production using SMRs without carbon capture is 10.4 tonnes of $CO_2$ emitted for each tonne of hydrogen produced. As such, direct replacement of natural hydrogen for hydrogen manufactured by SMR processes results in a $CO_2$ reduction of 10.4 tonnes $CO_2$/tonne $H_2$.

In power generation with gas turbines, hydrogen must displace the energy (btu) equivalent of natural gas. The energy density of hydrogen is 290 btu/cf or 51,682 btu/lb. By comparison, the energy density of natural gas is 983 btu/cf or 20,267 btu/lb, while the carbon intensity of natural gas is 52.91 kg $CO_2$/mmbtu $CH_4$ or 54.87 kg $CO_2$/mcf $CH_4$, or 3.5 kg $CO_2$/kg $CH_4$.

Because hydrogen is 2.6 times more energy dense per unit mass than natural gas, only 40‰ f the gross tonnage of fuel is required to achieve the same energy output. As such, burning one tonne of $H_2$ for power generation reduces natural gas consumption by about 2.6 tonnes, and thus $CO_2$ emissions by 9.1 tonnes.

Comparing natural hydrogen produced by enhanced hydrogen production reactions to hydrogen produced by electrolysis, the carbon reduction is a function of the carbon intensity of the power used in the electrolysis process. Although there may be large indirect emissions associated with electrolysis, there are no direct emissions. However, natural hydrogen produced by enhanced hydrogen production may lead to a direct emissions reduction for carbon dioxide, sulfur, or both sulfur and carbon dioxide as part of various EHP processes, including those that directly sequester carbon dioxide emissions, sulfur emissions, and combinations of carbon dioxide emissions and sulfur emissions permanently in mineral forms. With respect to carbon dioxide in instances where $H_2S$ and $CO_2$ are involved in the EHP process, there is a direct emissions reduction of about 10 tonnes of $CO_2$ emitted for each tonne of hydrogen produced, as compared to electrolytically produced hydrogen (or other forms of hydrogen generation). Integration of this process achieves net carbon negative hydrogen production.

Indirect Emissions Reduction: An analysis of the lifecycle carbon intensity of natural hydrogen using the Oil Production Greenhouse Gas Emissions Estimator ("OPGEE") has shown the lifecycle carbon intensity of natural hydrogen to be in the range of 0.1 to 0.4 tonnes $CO_2$/tonne $H_2$ with an additional emissions reduction equivalent to the mass of carbon dioxide mineralized along with sulfur by various sulfur-enhanced hydrogen production methods. Similar studies are not available for other methods of hydrogen production. However, using an average grid intensity of 0.5 tonnes $CO_2$/MWh, and given that electrolysis requires approximately 50 MWh/tonne $H_2$ produced, the indirect emissions associated with electrolysis are about 25 tonnes $CO_2$/tonne $H_2$ produced assuming grid power. Of course, electrolysis unit operators can purchase Renewable Energy Credits to synthetically reduce the carbon footprint of their power usage, but market recognition of this as a method for eliminating real time carbon emissions may not be permanent.

The realization of abundant natural hydrogen can achieve significant reductions in equivalent carbon emissions.

Natural hydrogen reservoirs and targets for the stimulation of subsurface hydrogen production may be found nearby many existing geothermal power plants. Some geothermal plants already have hydrogen making up a portion of their non-condensable gases vented from their systems. However, the methods and system described herein can capture the hydrogen from vent gases and utilize the same to increase output of a geothermal power plant.

The systems and methods described herein utilize the coincidence of subsurface hydrogen resources, the coincidence of subsurface formations from which hydrogen can be produced by enhanced hydrogen production processes, or other forms of synthetic hydrogen formation (e.g., electrolysis, pyrolysis) and geothermal power generation plants. Geothermal power plant performance is enhanced by integrating combustion of hydrogen produced from the above sources into operation of the power plant.

In some embodiments, wind electrolysis, solar electrolysis, hydropower electrolysis, SMR with carbon capture, traditional SMR, and methane pyrolysis may be located in close proximity to geothermal power plants and the hydrogen may be used to enhance the serviceable life and production capacity of existing geothermal plants.

A subset of geothermal plants (e.g., various fields in Iceland, the west coast of the United States, the Pacific Rim, or the East African Rift) are located in regions that tend to be associated with the presence of mafic rock, iron-rich rock, or iron-rich sediments. Geothermal power plants operate by two main methods: (1) Flash steam plants, where hot water and/or steam are extracted from the ground, flashed and run through a turbine, and then condensed and reinjected, or (2) Binary cycle plants, where hot water or brine is brought to the surface, heat exchanged with organic fluids, which are flashed and run through an organic Rankine cycle turbine and then condensed. The cooled water or brine can then be reinjected and moved slowly through the geothermal reservoir to provide pressure support or until it is produced again as hot brine.

It is noted that there is no requirement to provide or address the theory underlying the novel and groundbreaking processes, production rates, performance or other beneficial features and properties that are the subject of, or associated with, embodiments of the present disclosure. Nevertheless, various theories are provided in this specification to further advance the art in this important area, and in particular in the important area of hydrogen, dihydrogen sulfide, carbon dioxide, and helium exploration, production and downstream conversion or utilization. These theories put forth in this specification, and unless expressly stated otherwise, in no way limit, restrict or narrow the scope of protection to be afforded the claimed embodiments. It is further understood that the present disclosure may lead to new, and heretofore unknown theories to explain the conductivities, drainages, resource production, chemistries, and function-features of embodiments of the methods, articles, materials, devices, and system of the present disclosure; and such later developed theories shall not limit the scope of protection afforded the present disclosure.

Other embodiments than those specifically disclosed herein may be included without departing from its spirit or essential characteristics. The described embodiments are to be considered in all respects only as illustrative and not restrictive. The various aspects and embodiments disclosed herein are for purposes of illustration and are not intended to be limiting. The various embodiments of devices, systems, activities, methods, and operations set forth in this specification may be used with, in, or by, various processes, industries, and operations, in addition to those embodiments of the Figures and disclosed in this specification. The various embodiments of devices, systems, methods, activities, and operations set forth in this specification may be used with: other processes, industries, and operations that may be developed in the future: with existing processes, industries, and operations, which may be modified, in-part, based on the teachings of this specification; and with other types of gas recovery and valorization systems and methods. Further, the various embodiments of devices, systems, activities, methods, and operations set forth in this specification may be used with each other in different and various combinations. Thus, for example, the configurations provided in the various embodiments of this specification may be used with each other. For example, the components of an embodiment having A, A', and B and the components of an embodiment having A", C, and D can be used with each other in various combination, e.g., A, C, D, and A; A", C, and D, etc., in accordance with the teaching of this specification. Thus, the scope of protection afforded the present inventions should not be limited to a particular embodiment, configuration or arrangement that is set forth in a particular embodiment, example, or in an embodiment in a particular Figure.

Terms of degree (e.g., "about," "substantially," "generally," etc.) indicate structurally or functionally insignificant variations. In an example, when the term of degree is included with a term indicating quantity, the term of degree is interpreted to mean ±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

What is claimed is:

1. A method for assessing a molecular composition of a fluid, comprising:
  analyzing a proportion of the fluid derived from a source to determine an origination of hydrogen in the fluid, wherein the origination of hydrogen comprises at least one of a geologic hydrogen, a subsurface formation, steam methane reformation, coal, pyrolysis, autothermal reformation, chemical looping of gases, or electrolysis;
  quantifying the proportion of the fluid; and
  assessing a relationship of chemical species within the fluid to validate the origination of hydrogen of the fluid by comparing the chemical species within the fluid with statistical data of chemical species of known sources;
  quantifying or apportioning the source of hydrogen in the fluid; and
  certifying the source of hydrogen in the fluid, wherein the source of hydrogen is derived from natural gas pipelines, hydrogen pipelines, oil pipelines, water pipelines, railcars, trucks, industrial and storage facilities, springs, surface seeps, subsurface reservoirs, or boreholes.

2. The method of claim 1, wherein the fluid comprises a gas or a mixture of gases including at least one of hydrogen, helium, a noble gas, ammonia, carbon dioxide, dihydrogen sulfide, nitrogen, or hydrocarbon gases.

3. The method of claim 1, wherein analyzing a proportion of the fluid comprises measuring elements, molecules, isotopes, or isotopic ratios of the fluid.

4. The method of claim 1, further comprising monitoring for leaks or gas emissions in the source of the fluid.

5. The method of claim 1, further comprising validating and certifying a proportion of carbon dioxide stored in a subsurface reservoir, including pore space or mineralization of the carbon dioxide stored in a subsurface reservoir.

6. The method of claim 1, further comprising determining a residence time of the fluid in a subsurface formation, wherein determining the residence time includes:
  analyzing a concentration of a noble gas and isotopic compositions of water, carbon dioxide, or other subsurface fluids;
  analyzing a timing of crystallization or recrystallization of minerals to derive a timing of hydrogen generation in the subsurface formation using a rock sample core, cutting, or outcrop; and
  analyzing the core, cutting, or outcrop to measure a uranium, thorium, potassium, or mineral composition and crustal noble gas content in the mineral to derive the timing of hydrogen generation in the subsurface formation.

7. The method of claim 6, further comprising distinguishing the source of the hydrogen generation by the timing of hydrogen generation in the subsurface formation.

8. The method of claim 1, further comprising determining a gas saturation and gas to water ratio with respect to hydrogen, methane, natural gas, or carbon dioxide in the fluid, wherein the fluid is collected at the surface or from a subsurface formation.

9. A method for analyzing an isotopic composition, the method comprising:
  analyzing a fluid to determine an origination of hydrogen in the fluid, wherein the origination of hydrogen comprises at least one of a geologic hydrogen, a subsurface formation, steam methane reformation, coal, pyrolysis, autothermal reformation, chemical looping of gases, or electrolysis;
  analyzing the fluid to determine a proportion of hydrogen feedstock derived from the origination of hydrogen in the fluid by comparing chemical species within the fluid with statistical data of chemical species of known sources;
  quantifying the proportion of hydrogen feedstock derived from a source of the fluid; and
  certifying the proportion of hydrogen feedstock derived from the source of the fluid, wherein the source of the fluid is one of natural gas pipelines, hydrogen pipelines, oil pipelines, water pipelines, railcars, trucks, industrial and storage facilities, springs, surface seeps, subsurface reservoirs, or boreholes.

10. The method of claim 9, wherein the fluid comprises at least one of hydrogen, helium, dihydrogen sulfide, nitrogen, methane or hydrocarbon gas, water, methanol, synthetic fuels, ammonia, or carbon dioxide.

11. The method of claim 9, further comprising validating and certifying a proportion of carbon dioxide stored in a subsurface reservoir including pore space or mineralization.

12. The method of claim 9, further comprising determining carbon feedstock in a hydrogen carrier and quantifying a proportion of carbon derived from the hydrogen carrier, wherein the hydrogen carrier comprises at least one of coal combustion, natural gas combustion, biomass incineration, ammonia syntheses, steel manufacturing, chemical synthesis, waste incineration, or atmospheric capture.

13. The method of claim 9, wherein analyzing the fluid includes comparing a measurement of an isotopic ratio of hydrogen from a sample with data for isotopic ratios of hydrogen for known samples of hydrogen.

14. The method of claim 9, further comprising certifying a source of hydrogen in at least one of a natural gas pipeline, hydrogen pipeline, oil pipeline, water pipeline, railcar, truck, or industrial facility.

15. The method of claim 9, further comprising determining a composition of matter for hydrogen using an isotopic composition of hydrogen to determine, quantify, and validate a proportion of hydrogen, methane or other natural gases, or carbon dioxide derived from the source.

16. A system for determining information including one or more characteristics of water, hydrogen, methane or other natural gases, carbon dioxide, or noble gases, the system comprising:
  chemical analysis equipment configured to determine the information comprising at least one of:
    a molecular composition of a fluid including one or more of the hydrogen, methane or other natural gases, or carbon dioxide;

a gas saturation and gas to water ratio with respect to the hydrogen, methane or other natural gases, or carbon dioxide;

a residence time of hydrogen or carbon dioxide in the fluid;

a mass of water;

a concentration of helium and other noble gases and isotopic concentrations of the helium or other noble gases;

a source of hydrogen, carbon dioxide, or natural gas by comparing chemical species within the fluid with statistical data of chemical species of known sources; and an origination of hydrogen in the fluid, wherein the origination of hydrogen comprises at least one of a geologic hydrogen, a subsurface formation, steam methane reformation, coal, pyrolysis, autothermal reformation, chemical looping of gases, or electrolysis; and a computing device operably connected to the chemical analysis equipment, the computing device being configured to electronically communicate the information to a remote computing device.

17. The system of claim 16, wherein the remote computing device is operably coupled to the computing device and the remote computing device is configured to determine:

a source of the fluid;

a proportion of hydrogen feedstock derived from the source of the fluid; and a quantity of the proportion of hydrogen feedstock derived from the source of the fluid.

18. The system of claim 16, wherein the chemical analysis equipment includes at least one of an isotope ratio mass spectrometer, a cavity ring down spectroscopy apparatus, a residual gas analyzer, a quadrupole mass spectrometer, a radon detector, a scintillation counter, a gas chromatograph, a gas chromatograph fitted with a flame ionizing detector, or a thermal conductivity detector.

19. The method of claim 1, further comprising issuing, in response to certifying the fluid, a certificate for a tax credit.

20. The method of claim 9, further comprising issuing, in response to certifying the fluid, a certificate for a tax credit.

* * * * *